United States Patent
Jeong et al.

(10) Patent No.: US 10,544,140 B2
(45) Date of Patent: Jan. 28, 2020

(54) PHARMACEUTICAL COMPOSITION CONTAINING, AS ACTIVE INGREDIENT, 7-AZAINDOLIN-2-ONE DERIVATIVE OR PHARMACEUTICALLY ACCEPTABLE SALT THEREOF

(71) Applicant: LG CHEM, LTD., Seoul (KR)

(72) Inventors: Byeong-Seon Jeong, Daegu (KR); Jung-Ae Kim, Daegu (KR); Tae-gyu Nam, Suwon-si (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/775,312

(22) PCT Filed: Oct. 31, 2016

(86) PCT No.: PCT/KR2016/012409
§ 371 (c)(1),
(2) Date: May 10, 2018

(87) PCT Pub. No.: WO2017/082569
PCT Pub. Date: May 18, 2017

(65) Prior Publication Data
US 2018/0370964 A1   Dec. 27, 2018

(30) Foreign Application Priority Data

Nov. 12, 2015 (KR) .......................... 10-2015-0158695

(51) Int. Cl.
| | |
|---|---|
| *C07D 471/04* | (2006.01) |
| *A61K 31/437* | (2006.01) |
| *A61K 31/4439* | (2006.01) |
| *A61P 35/00* | (2006.01) |
| *A61P 35/04* | (2006.01) |

(52) U.S. Cl.
CPC .......... *C07D 471/04* (2013.01); *A61K 31/437* (2013.01); *A61K 31/4439* (2013.01); *A61P 35/00* (2018.01); *A61P 35/04* (2018.01)

(58) Field of Classification Search
CPC ........................... A61K 31/437; C07D 471/04
See application file for complete search history.

(56) References Cited

U.S. PATENT DOCUMENTS

2002/0183319 A1   12/2002 Liang et al.
2014/0275033 A1   9/2014 Li et al.

FOREIGN PATENT DOCUMENTS

| CN | 104876928 A | 9/2015 |
| EP | 2 292 613 A1 | 3/2011 |
| WO | 2013-112959 A1 | 8/2013 |
| WO | 2014-085795 A1 | 6/2014 |

OTHER PUBLICATIONS

Shah et al. (Organic & Biomolecular Chemistry, 2016, vol. 14, pp. 4829-4841).*
Shah et al. (Organic & Biomolecular Chemistry, 2016, 14(21), pp. 4829-4841).*
Search Report issued for PCT Application No. PCT/KR2016/012409 dated Feb. 2, 2017, 5 pages.
Supplemental European Search Report issued for European Patent Application No. 16864495.3 dated Oct. 30, 2018, 10 pages.
H.J. Lee et al., "Pyridoxine-derived bicyclic amido-, ureido-, and carbamato-pyridinols: synthesis and antiangiogenic activites," Organic & Biomolecular Chemistry, 2014, vol. 12, No. 43, pp. 8702-8710.
D.G. Kim et al., "6-Amino-2,4,5-trimethylpyridin-3-ols: A new general synthetic route and antiangiogenic activity," European Journal of Medicinal Chemistry, 2014, vol. 78, pp. 126-139.
M. Wang et al., "Synthesis and antitumor activity of 5-(5-halogenated-2-oxo-1H-pyrrolo[2,3-b]pyridin-(3Z)-ylidenemethyl)-2,4-dimethyl-1H-pyrrole-3-carboxamides," Bioorganic & Medicinal Chemistry Letters, 2015, vol. 25, No. 14, pp. 2782-2787.
Lv Kai et al., "Synthesis and in vitro antitumor activity of 1-(3-dimethylamino)propyl indolin-2-one derivatives," Medicinal Chemistry Research, 2012, vol. 22, No. 4, pp. 1723-1729.
Lv Kai et al., "Synthesis and antitumor activity of 5-[1-(3-dimethylamino)propyl)-5-halogenated-2oxoindolin-(3Z)-ylidenemethyl]-2,4-dimethyl-1H-pyrrole-3-carboxamides," Bioorganic & Medicinal Chemistry Letters, 2011, vol. 21, No. 10, pp. 3062-3065.
Patricia A. Eisenach, et al., "MT1-MMP regulates VEGF-A expression through a complex with VEGFR-2 and Src," Journal of Cell Science, 2010, vol. 123, 4182-4193.

(Continued)

*Primary Examiner* — Susanna Moore
(74) *Attorney, Agent, or Firm* — Rothwell, Figg, Ernst & Manbeck, P.C.

(57) ABSTRACT

7-azaindolin-2-one derivatives of Formula 1

[Formula 1]

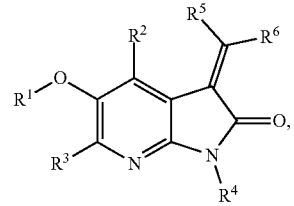

or pharmaceutically acceptable salts thereof, a pharmaceutical composition comprising them for preventing or treating a cancer, and a method for preparing them.

8 Claims, No Drawings

(56) References Cited

OTHER PUBLICATIONS

P.J. Polverini, "The Pathophysiology of Angiogenesis," Critical Reviews in Oral Biology & Medicine, 1995, vol. 6 issue: 3, pp. 230-247.

Rafi Mazor, et al., "Matrix Metalloproteinase-1-mediated Up-regulation of Vascular Endothelial Growth Factor-2 in Endothelial Cells," The Journal of Biological Chemistry, 2013, vol. 288, No. 1, pp. 598-607.

Estefanía Ugarte-Berzal, et al., "VEGF/VEGFR2 interaction down-regulates matrix metalloproteinase-9 via STAT1 activation and inhibits B chronic lymphocytic leukemia cell migration," Blood, 2010, vol. 115, No. 4.

\* cited by examiner

PHARMACEUTICAL COMPOSITION CONTAINING, AS ACTIVE INGREDIENT, 7-AZAINDOLIN-2-ONE DERIVATIVE OR PHARMACEUTICALLY ACCEPTABLE SALT THEREOF

CROSS-REFERENCE TO RELATED APPLICATION

This application is a 35 U.S.C. 371 National Phase Entry Application from PCT/KR2016/012409, filed Oct. 31, 2016, which claims the benefit of priority from Korean Patent Application No. 10-2015-0158695 filed on Nov. 12, 2015 with the Korean Intellectual Property Office, the disclosures of which are incorporated herein by reference in their entirety.

TECHNICAL FIELD

The present invention relates to a pharmaceutical composition for the prevention or treatment of cancer disease, comprising 7-azaindolin-2-one derivative or a pharmaceutically acceptable salt thereof as an active ingredient.

BACKGROUND ART

One of the major causes for death of cancer patients is metastasis of cancer, and it is also the reason why chemotherapies or immunotherapies currently in clinical use cannot greatly contribute to an increase in the viability of cancer patients.

Most solid tumor metastases show that cancer cells proliferate at the site where cancer cells first appear, and as the cancer mass grows larger, the tumor is provided with nutrition and oxygen needed for growth and proliferation via new blood vessels. Then, the cancer cells are separated from the cancer mass, migrate to other parts of the body through the blood vessels, and then settle in secondary sites, where cell proliferation again occurs. That is, the new blood vessels that penetrate into the tumor give metastatic cancer cells the opportunity to enter the blood circulation system, which is a crucial help for cancer cells to metastasize (Non-patent Document 1).

Signaling molecules that play a key role in growth and metastasis of cancers as well as angiogenesis are growth factors including VEGF (vascular endothelial growth factor) and receptors thereof. Receptor tyrosine kinase (RTK), which is a key part of growth factor receptors, is involved in various cell activities such as cell survival, differentiation, migration, proliferation and the like. Such RTK plays a key role in the growth and malignant process of cancers by abnormal regulation and overactivation in various cancer cells. Various kinds of RTK, including VEGF receptor 2 (KDR) tyrosine kinase, regulate survival and proliferation of cancer cells, and also induce angiogenesis by facilitating proliferation and migration of vascular endothelial cells, and tubular formation. In the case of cancers, various kinds of growth factors in addition to VEGF are secreted to stimulate RTK of cancer cells and vascular endothelial cells, thereby resulting in growth of tumors and metastasis via blood vessels. As such, in the case of inhibiting KDR tyrosine kinase only, cancer cells show resistance thereon, and growth of inhibited cancer is resumed. Therefore, inhibition of receptor RTK for various kinds of growth factors is an efficient strategy for developing anticancer drugs. The representative example is sunitinib (trademark: Sutent [sunitinib malate]), which is a multi-targeted RTK inhibitor.

In order for cancer cells to migrate into other parts of the body via blood vessels, cancer cells must go through an invasion process. For this, cancer cells secrete over-expressed proteinases to degrade the extracellular matrix. Such degradation enzymes include matrix metalloproteinases (MMPs), cathepsins and various proteinases. There are many types of MMPs, and MMPs are one of the most important enzyme groups that mediate invasion and metastasis of cancers by secreting from cells such as fibroblasts and macrophages in surrounding tissues of cancers, as well as cancer cells. Intercellular signaling by binding of VEGF to VEGFR2 inhibits the expression of MMP (Non-patent Document 2). In addition, MMP is involved in regulating the expression of VEGF or VEGFR2 (Non-patent Documents 3 and 4).

Integrated regulation of cancer growth, angiogenesis and metastasis would ultimately be an efficient way for treating cancer and decreasing the death rate due to metastasis of cancer. In addition, it would be efficient to select targeted molecules such as RTK which is involved in the overall processes of cancer growth, angiogenesis and cancer cell invasion/metastasis. Furthermore, the matter—that conventional anticancer drugs inhibiting cancer growth cause a toxicity problem due to long-term administration—requires the development of drugs that are efficient anticancer agents having inhibitory effect against metastasis and low toxicity.

NON-PATENT DOCUMENTS

1. Folkman and Tyler, Cancer Invasion and metastasis, Biologic mechanisms and Therapy (S. B. Day ed.) Raven press, New York, pp 94-103, 1977; Polverini P J, Crit. Rev. Oral. Biol. Med., 1995, 6, 230-247.
2. Ugarte-Berzal E. et al., Blood 2010, 115(4):846-849.
3. Mazor R. et al., The Journal of Biological Chemistry 2013, 288, 598-607.
4. Eisenach P. A. et al., Journal of Cell Science 2013, 123: 4182-4193.

DISCLOSURE OF INVENTION

Technical Problem

The present inventors confirmed that 7-azaindolin-2-one derivatives having certain structures or pharmaceutically acceptable salts thereof show excellent inhibitory effect against cancer growth, thereby completing the present invention.

Therefore, the object of the present invention is the provision of a pharmaceutical composition for the prevention or treatment of cancer disease, comprising a 7-azaindolin-2-one derivative or a pharmaceutically acceptable salt thereof as an active ingredient.

Solution to Problem

To accomplish the object, the present invention provides a compound represented by the following Formula 1 or a pharmaceutically acceptable salt thereof:

[Formula 1]

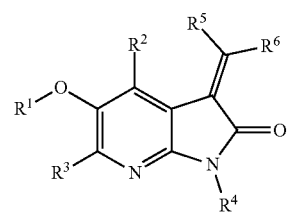

wherein, $R^1$, $R^4$ and $R^5$ each independently represent any one selected from the group consisting of hydrogen; halogen; and $C_1$-$C_4$ alkyl;

$R^2$ and $R^3$ each independently represent $C_1$-$C_4$ alkyl;

$R^6$ represents any one selected from the group consisting of hydrogen; $C_1$-$C_{12}$ alkyl; $C_2$-$C_{12}$ alkenyl; $C_6$-$C_{12}$ aryl; and $C_3$-$C_{12}$ heteroaryl containing 1 to 3 heteroatoms;

wherein the $C_1$-$C_{12}$ alkyl or the $C_2$-$C_{12}$ alkenyl is unsubstituted or substituted with $C_6$-$C_{12}$ aryl;

the $C_6$-$C_{12}$ aryl is unsubstituted or substituted with one or more substituents selected from the group consisting of halogen; —$NO_2$; $C_1$-$C_4$ alkyl; —$OR^{11}$; and —$NR^{20}R^{21}$;

the $C_3$-$C_{12}$ heteroaryl is unsubstituted or substituted with one or more substituents selected from the group consisting of $C_1$-$C_4$ alkyl; —$C(O)R^{14}$; —$C(O)OR^{15}$; and —$C(O)NR^{22}R^{23}$;

$R^{11}$, $R^{14}$ and $R^{15}$ each independently represent any one selected from the group consisting of hydrogen; and $C_1$-$C_4$ alkyl;

$R^{20}$ to $R^{23}$ each independently represent any one selected from the group consisting of hydrogen; and $C_1$-$C_6$ alkyl, or $R^{22}$ and $R^{23}$ taken together may form $C_3$-$C_8$ heteroaryl containing 1 to 3 heteroatoms;

wherein the $C_1$-$C_4$ alkyl and the $C_3$-$C_8$ heteroaryl of $R^{11}$, $R^{14}$, $R^{15}$, and $R^{20}$ to $R^{23}$ are each independently unsubstituted or substituted with one or more substituents selected from the group consisting of $C_1$-$C_4$ alkyl; and —$NR^{24}R^{25}$;

$R^{24}$ and $R^{25}$ each independently represent any one selected from the group consisting of hydrogen; and $C_1$-$C_4$ alkyl, or $R^{24}$ and $R^{25}$ taken together may form $C_3$-$C_8$ heteroaryl containing 1 to 3 heteroatoms.

In addition, the present invention provides a method for preparing a compound of the following Formula 1 comprising reacting a compound of the following Formula 2 with a compound of the following Formula 3:

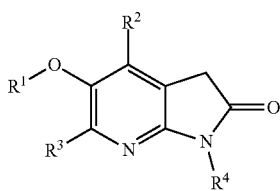

[Formula 2]

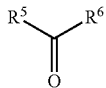

[Formula 3]

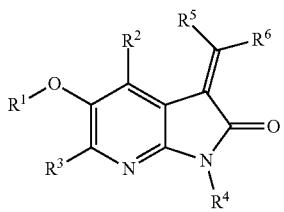

[Formula 1]

In addition, the present invention provides a pharmaceutical composition for the prevention or treatment of cancer disease, comprising the above-mentioned compound or a pharmaceutically acceptable salt thereof as an active ingredient.

In addition, the present invention provides a pharmaceutical composition for the prevention or inhibition of cancer invasion or cancer metastasis, comprising the above-mentioned compound or a pharmaceutically acceptable salt thereof as an active ingredient.

Effects of the Invention

The 7-azaindolin-2-one derivatives or pharmaceutically acceptable salts thereof according to the present invention can be favorably used as a medicament for inhibiting cancer growth and cancer metastasis.

BEST MODES FOR CARRYING OUT THE INVENTION

Hereinafter, the present invention is described in more detail.

The present invention provides a compound represented by the following Formula 1 (hereinafter referred to as the compound of Formula 1) or a pharmaceutically acceptable salt thereof:

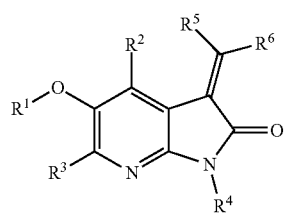

[Formula 1]

wherein, $R^1$, $R^4$ and $R^5$ each independently represent any one selected from the group consisting of hydrogen; halogen; and $C_1$-$C_4$ alkyl;

$R^2$ and $R^3$ each independently represent $C_1$-$C_4$ alkyl;

$R^6$ represents any one selected from the group consisting of hydrogen; $C_1$-$C_{12}$ alkyl; $C_2$-$C_{12}$ alkenyl; $C_6$-$C_{12}$ aryl; and $C_3$-$C_{12}$ heteroaryl containing 1 to 3 heteroatoms;

wherein the $C_1$-$C_{12}$ alkyl or the $C_2$-$C_{12}$ alkenyl is unsubstituted or substituted with $C_6$-$C_{12}$ aryl;

the $C_6$-$C_{12}$ aryl is unsubstituted or substituted with one or more substituents selected from the group consisting of halogen; —$NO_2$; $C_1$-$C_4$ alkyl; —$OR^{11}$; and —$NR^{20}R^{21}$;

the $C_3$-$C_{12}$ heteroaryl is unsubstituted or substituted with one or more substituents selected from the group consisting of $C_1$-$C_4$ alkyl; —$C(O)R^{14}$; —$C(O)OR^{15}$; and —$C(O)NR^{22}R^{23}$;

$R^{11}$, $R^{14}$ and $R^{15}$ each independently represent any one selected from the group consisting of hydrogen; and $C_1$-$C_4$ alkyl;

$R^{20}$ to $R^{23}$ each independently represent any one selected from the group consisting of hydrogen; and $C_1$-$C_6$ alkyl, or $R^{22}$ and $R^{23}$ taken together may form $C_3$-$C_8$ heteroaryl containing 1 to 3 heteroatoms;

wherein the $C_1$-$C_4$ alkyl and the $C_3$-$C_8$ heteroaryl of $R^{11}$, $R^{14}$, $R^{15}$, and $R^{20}$ to $R^{23}$ are each independently unsubstituted or substituted with one or more substituents selected from the group consisting of $C_1$-$C_4$ alkyl; and —$NR^{24}R^{25}$;

$R^{24}$ and $R^{25}$ each independently represent any one selected from the group consisting of hydrogen; and $C_1$-$C_4$ alkyl, or $R^{24}$ and $R^{25}$ taken together may form $C_3$-$C_8$ heteroaryl containing 1 to 3 heteroatoms.

In the present invention, the compound of Formula 1 may be referred to as 7-azaindolin-2-one derivative.

In addition, the terms used in the definitions of substituents for the compound according to the present invention are as follows.

Unless indicated otherwise, the term "alkyl" refers to straight, branched or cyclic saturated hydrocarbons having the indicated number of carbon atoms.

Unless indicated otherwise, the term "alkenyl" refers to hydrocarbons having the indicated number of carbon atoms, at least two (2) carbon atoms and at least one (1) carbon-carbon double bond.

The term "halogen" refers to fluoro (F), chloro (Cl), bromo (Br) or iodo (I).

Unless indicated otherwise, the term "heterocycle" refers to a non-aromatic saturated hydrocarbon ring, or a single ring and a fused ring as an aromatic ring containing a heteroatom of oxygen (O), nitrogen (N) and sulfur (S).

Unless indicated otherwise, the term "aryl" refers to a monovalent or divalent aromatic group comprising a 5-membered and 6-membered monocyclic aromatic group.

The term "heteroaryl" refers to a monovalent or divalent aromatic group comprising a 5-membered and 6-membered monocyclic aromatic group, which contains 1 to 3 heteroatoms independently selected from nitrogen (N), oxygen (O) and sulfur (S). Examples of heteroaryl include, but are not limited to, furanyl, pyrrolyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, pyrimidinyl, isoquinolinyl, carbazolyl, benzoxazolyl, benzodioxazolyl, benzothiazolyl, benzoimidazolyl, benzothiophenyl, triazinyl, phthalazinyl, quinolinyl, indolyl, benzofuranyl, purinyl and indolizinyl.

The term "pharmaceutical composition" refers to a mixture of the compound according to the present invention or a physiologically/pharmaceutically acceptable salt thereof or a prodrug thereof, and other chemical components, such as physiologically/pharmaceutically acceptable carriers and excipients. The purpose of a pharmaceutical composition is to facilitate administration of a compound to an organism.

In addition, the compound of Formula 1 may act as a prodrug. The term "prodrug" refers to a substance that is converted into a parent drug in the body. Because prodrugs are sometimes easier to administer than parent drugs, they are often useful. For example, even if a parent drug is not bioavailable by oral administration, its prodrug can be bioavailable by oral administration. In addition, prodrugs may show improved solubility as compared with parent drugs in a pharmaceutical composition.

The term "physiologically/pharmaceutically acceptable carrier" refers to a carrier or diluent that does not cause significant irritation to an organism and does not abrogate the biological activity and properties of the administered compound.

The term "physiologically/pharmaceutically acceptable excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

The terms "treat," "treating" and "treatment" refer to a method of alleviating or eliminating the diseases according to the present invention and symptoms associated therewith. With respect to cancer in particular, these terms simply mean to increase the survival rate of the individual suffering from the cancer or to reduce one or more symptoms of the disease.

The term "organism" means all living things made up of at least one or more cells. Living organisms can be as simple as eukaryotic single cells or can be as complex as mammals, including humans.

The term "therapeutically effective amount" refers to the amount of a compound administered which can alleviate to some extent one or more of the symptoms of the disease being treated. With regard to the treatment of cancer, a therapeutically effective amount refers to the amount having the following effect:

(1) Reducing the size of the tumor;

(2) Inhibiting (that is, slowing to some extent, preferably stopping) tumor metastasis;

(3) Inhibiting to some extent (that is, slowing to some extent, preferably stopping) tumor growth; and/or (4) Alleviating to some extent (or, preferably eliminating) one or more symptoms associated with cancer.

In one embodiment of the present invention, in the compounds of Formula 1, $R^1$, $R^4$ and $R^5$ may be hydrogen; and $R^2$ and $R^3$ may be methyl.

In addition, in one embodiment, in the compounds of Formula 1, $R^6$ may represent:

hydrogen; or $C_1$-$C_{12}$ alkyl or $C_2$-$C_{12}$ alkenyl which is unsubstituted or substituted with $C_6$-$C_{12}$ aryl, wherein said $C_6$-$C_{12}$ aryl is unsubstituted or substituted with one or more substituents selected from the group consisting of OH and methoxy; or $C_6$-$C_{12}$ aryl which is unsubstituted or substituted with one or more substituents selected from the group consisting of halogen, —$NO_2$, OH, methoxy, methyl, ethyl, propyl, methylamine, ethylamine, dimethylamine and diethylamine; or $C_3$-$C_{12}$ heteroaryl containing 1 to 3 heteroatoms which is unsubstituted or substituted with one or more substituents selected from the group consisting of methyl; ethyl; —C(O)$OR^{15}$; and —C(O)$NR^{22}R^{23}$;

$R^{15}$ represents hydrogen, methyl or ethyl;

$R^{22}$ and $R^{23}$ each independently represent hydrogen; or methyl or ethyl, which is unsubstituted or substituted with one or more substituents selected from the group consisting of methylamine, ethylamine, dimethylamine, diethylamine and piperidine; or $R^{22}$ and $R^{23}$ taken together may form cyclohexane, piperazine, piperidine, pyrrolidine or morpholine unsubstituted or substituted with methyl.

In addition, in one embodiment, in the compounds of Formula 1, $R^6$ may represent:

$C_1$-$C_8$ alkyl which is unsubstituted or substituted with one or more phenyls; or $C_2$-$C_8$ alkenyl which is unsubstituted or substituted with phenyl, wherein said phenyl is unsubstituted or substituted with one or more substituents selected from the group consisting of OH and methoxy; or $C_6$-$C_{10}$ aryl which is unsubstituted or substituted with one or more substituents selected from the group consisting of halogen, —$NO_2$, OH, methoxy, methyl, ethyl, dimethylamine and diethylamine; or $C_3$-$C_{10}$ heteroaryl containing 1 to 3 heteroatoms which is unsubstituted or substituted with one or more substituents selected from the group consisting of methyl; ethyl; —C(O)$OR^{15}$; and —C(O)$NR^{22}R^{23}$;

$R^{15}$ represents hydrogen, methyl or ethyl;

$R^{22}$ and $R^{23}$ each independently represent hydrogen; or methyl or ethyl, which is unsubstituted or substituted with one or more substituents selected from the group consisting of methylamine, ethylamine, dimethylamine, diethylamine and piperidine; or $R^{22}$ and $R^{23}$ taken together may form cyclohexane, piperazine, piperidine, pyrrolidine or morpholine unsubstituted or substituted with methyl.

More specifically, the compound of Formula 1 according to the present invention may be 3-alkylidene-5-hydroxy-1H-pyrrolo[2,3-b]pyridine-2(3H)-one derivatives.

The derivatives may be any one selected from the group consisting of the following compounds represented by Formulas I-01 to I-46 as shown in Table 1 below.

TABLE 1

| No. | Structure | Chemical Name |
|---|---|---|
| I-01 | 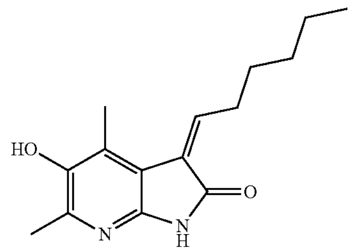 [SMILES: CCCCC/C=C1\C(=O)Nc2nc(C)c(O)c(C)c21] | (Z)-3-Hexylidene-5-hydroxy-4,6-dimethyl-1H-pyrrolo[2,3-b]pyridin-2(3H)-one |
| I-02 | 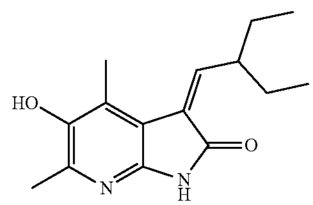 [SMILES: CCC(/C=C1\C(=O)Nc2nc(C)c(O)c(C)c21)CC] | (Z)-3-(2-Ethylbutylidene)-5-hydroxy-4,6-dimethyl-1H-pyrrolo[2,3-b]pyridin-2(3H)-one |
| I-03 | 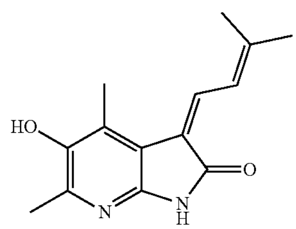 [SMILES: CC(C)=C/C=C1\C(=O)Nc2nc(C)c(O)c(C)c21] | (Z)-5-Hydroxy-4,6-dimethyl-3-(3-methylbut-2-enylidene)-1H-pyrrolo[2,3-b]pyridin-2(3H)-one |
| I-04 | 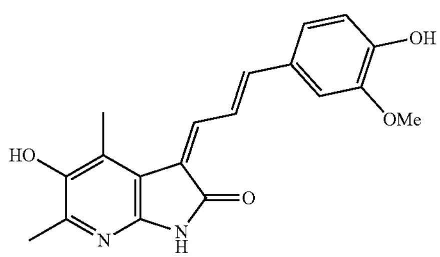 [SMILES: COc1cc(/C=C/C=C2\C(=O)Nc3nc(C)c(O)c(C)c32)ccc1O] | (Z)-5-Hydroxy-3-((E)-3-(4-hydroxy-3-methoxyphenyl)allylidene)-4,6-dimethyl-1H-pyrrolo[2,3-b]pyridin-2(3H)-one |
| I-05 | 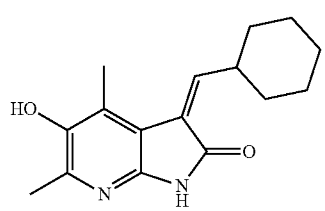 [SMILES: Cc1nc2c(c(C)c1O)/C(=C/C1CCCCC1)C(=O)N2] | (Z)-3-(Cyclohexylmethylene)-5-hydroxy-4,6-dimethyl-1H-pyrrolo[2,3-b]pyridin-2(3H)-one |
| I-06 | 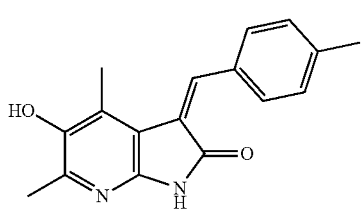 [SMILES: Cc1ccc(/C=C2\C(=O)Nc3nc(C)c(O)c(C)c32)cc1] | (Z)-5-Hydroxy-4,6-dimethyl-3-(4-methylbenzylidene)-1H-pyrrolo[2,3-b]pyridin-2(3H)-one |

TABLE 1-continued

| No. | Structure | Chemical Name |
|---|---|---|
| I-07 | 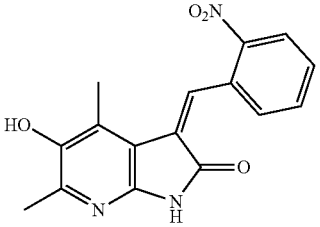 [SMILES: Cc1nc2c(c(C)c1O)/C(=C/c1ccccc1[N+](=O)[O-])C(=O)N2] | (Z)-5-Hydroxy-4,6-dimethyl-3-(2-nitrobenzylidene)-1H-pyrrolo[2,3-b]pyridin-2(3H)-one |
| I-08 | 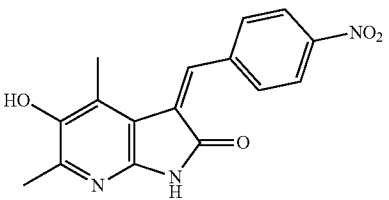 [SMILES: Cc1nc2c(c(C)c1O)/C(=C/c1ccc([N+](=O)[O-])cc1)C(=O)N2] | (Z)-5-Hydroxy-4,6-dimethyl-3-(4-nitrobenzylidene)-1H-pyrrolo[2,3-b]pyridin-2(3H)-one |
| I-09 | 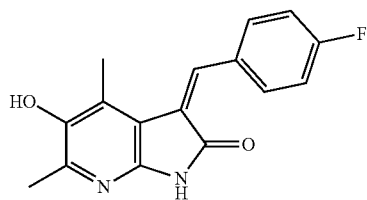 [SMILES: Cc1nc2c(c(C)c1O)/C(=C/c1ccc(F)cc1)C(=O)N2] | (Z)-3-(4-Fluorobenzylidene)-5-hydroxy-4,6-dimethyl-1H-pyrrolo[2,3-b]pyridin-2(3H)-one |
| I-10 | 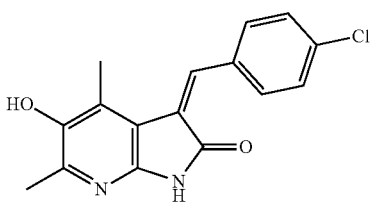 [SMILES: Cc1nc2c(c(C)c1O)/C(=C/c1ccc(Cl)cc1)C(=O)N2] | (Z)-3-(4-Chlorobenzylidene)-5-hydroxy-4,6-dimethyl-1H-pyrrolo[2,3-b]pyridin-2(3H)-one |
| I-11 | 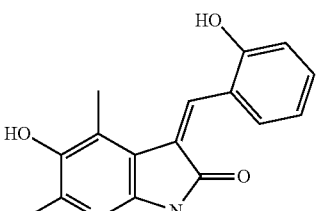 | (Z)-5-Hydroxy-3-(2-hydroxybenzylidene)-4,6-dimethyl-1H-pyrrolo[2,3-b]pyridin-2(3H)-one |
| I-12 | 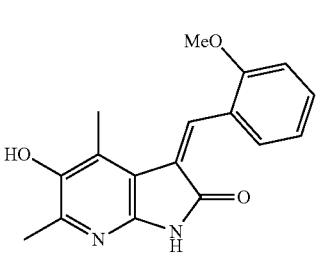 [SMILES: COc1ccccc1/C=C1\C(=O)Nc2nc(C)c(O)c(C)c21] | (Z)-5-hydroxy-3-(2-methoxybenzylidene)-4,6-dimethyl-1H-pyrrolo[2,3-b]pyridin-2(3H)-one |
| I-13 | 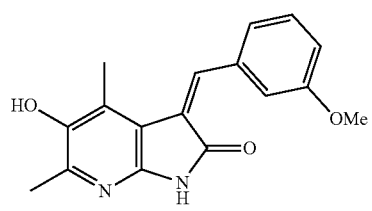 [SMILES: COc1cccc(/C=C2\C(=O)Nc3nc(C)c(O)c(C)c32)c1] | (Z)-5-Hydroxy-3-(3-methoxybenzylidene)-4,6-dimethyl-1H-pyrrolo[2,3-b]pyridin-2(3H)-one |

TABLE 1-continued

| No. | Structure | Chemical Name |
|---|---|---|
| I-14 | 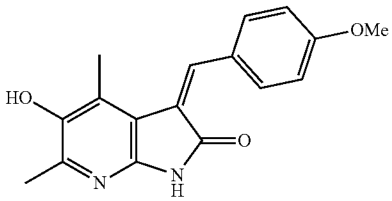 [SMILES: COc1ccc(/C=C2\C(=O)Nc3nc(C)c(O)c(C)c32)cc1] | (Z)-5-Hydroxy-3-(4-methoxybenzylidene)-4,6-dimethyl-1H-pyrrolo[2,3-b]pyridin-2(3H)-one |
| I-15 | 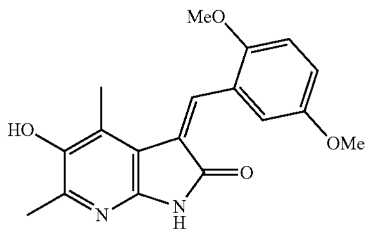 [SMILES: COc1ccc(OC)c(/C=C2\C(=O)Nc3nc(C)c(O)c(C)c32)c1] | (Z)-3-(2,5-Dimethoxybenzylidene)-5-hydroxy-4,6-dimethyl-1H-pyrrolo[2,3-b]pyridin-2(3H)-one |
| I-16 | 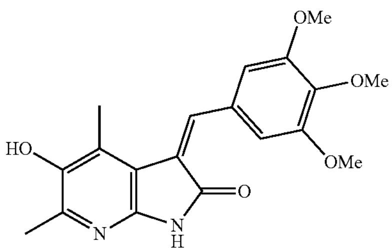 [SMILES: COc1cc(/C=C2\C(=O)Nc3nc(C)c(O)c(C)c32)cc(OC)c1OC] | (Z)-5-Hydroxy-4,6-dimethyl-3-(3,4,5-trimethoxybenzylidene)-1H-pyrrolo[2,3-b]pyridin-2(3H)-one |
| I-17 | 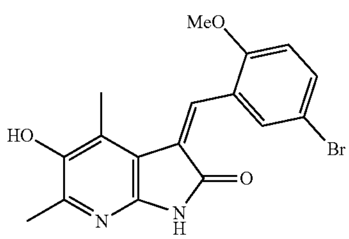 [SMILES: COc1ccc(Br)cc1/C=C1\C(=O)Nc2nc(C)c(O)c(C)c21] | (Z)-3-(5-bromo-2-methoxybenzylidene)-5-hydroxy-4,6-dimethyl-1H-pyrrolo[2,3-b]pyridin-2(3H)-one |
| I-18 | 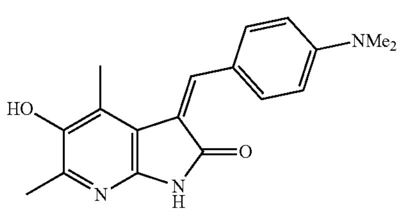 [SMILES: Cc1nc2c(c(C)c1O)/C(=C/c1ccc(N(C)C)cc1)C(=O)N2] | (Z)-3-(4-(Dimethylamino)benzylidene)-5-hydroxy-4,6-dimethyl-1H-pyrrolo[2,3-b]pyridin-2(3H)-one |
| I-19 | 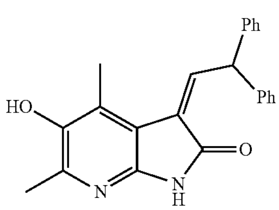 [SMILES: Cc1nc2c(c(C)c1O)/C(=C/C(c1ccccc1)c1ccccc1)C(=O)N2] | (Z)-3-(2,2-Diphenylethylidene)-5-hydroxy-4,6-dimethyl-1H-pyrrolo[2,3-b]pyridin-2(3H)-one |
| I-20 | 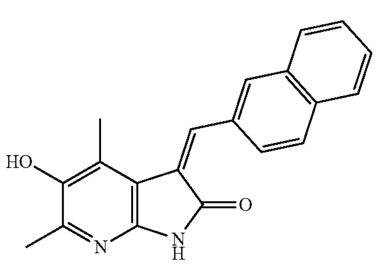 [SMILES: Cc1nc2c(c(C)c1O)/C(=C/c1ccc3ccccc3c1)C(=O)N2] | (Z)-5-Hydroxy-4,6-dimethyl-3-(naphthalen-2-ylmethylene)-1H-pyrrolo[2,3-b]pyridin-2(3H)-one |

TABLE 1-continued

| No. | Structure | Chemical Name |
|---|---|---|
| I-21 | 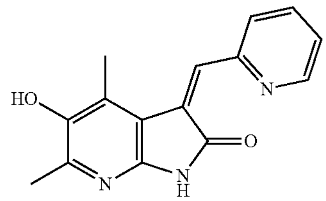 [SMILES: Cc1nc2c(c(C)c1O)/C(=C/c1ccccn1)C(=O)N2] | (Z)-5-Hydroxy-4,6-dimethyl-3-(pyridin-2-ylmethylene)-1H-pyrrolo[2,3-b]pyridin-2(3H)-one |
| I-22 | 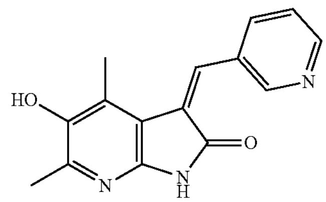 | (Z)-5-Hydroxy-4,6-dimethyl-3-(pyridin-3-ylmethylene)-1H-pyrrolo[2,3-b]pyridin-2(3H)-one |
| I-23 | 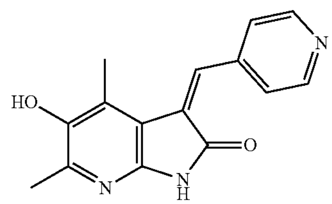 [SMILES: Cc1nc2c(c(C)c1O)/C(=C/c1ccncc1)C(=O)N2] | (Z)-5-Hydroxy-4,6-dimethyl-3-(pyridin-4-ylmethylene)-1H-pyrrolo[2,3-b]pyridin-2(3H)-one |
| I-24 | 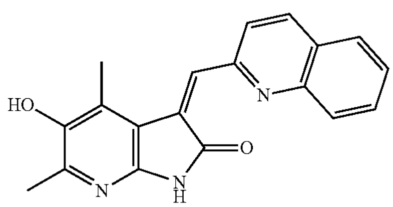 [SMILES: Cc1nc2c(c(C)c1O)/C(=C/c1ccc3ccccc3n1)C(=O)N2] | (Z)-5-Hydroxy-4,6-dimethyl-3-(quinolin-2-ylmethylene)-1H-pyrrolo[2,3-b]pyridin-2(3H)-one |
| I-25 | 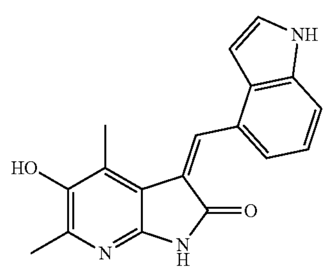 [SMILES: Cc1nc2c(c(C)c1O)/C(=C/c1cccc3[nH]ccc13)C(=O)N2] | (Z)-3-((1H-Indol-4-yl)methylene)-5-hydroxy-4,6-dimethyl-1H-pyrrolo[2,3-b]pyridin-2(3H)-one |
| I-26 | 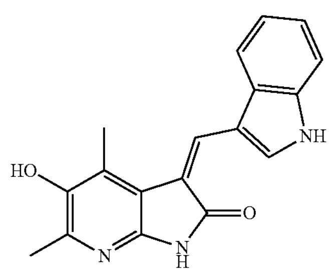 [SMILES: Cc1nc2c(c(C)c1O)/C(=C/c1c[nH]c3ccccc13)C(=O)N2] | (Z)-3-((1H-Indol-3-yl)methylene)-5-hydroxy-4,6-dimethyl-1H-pyrrolo[2,3-b]pyridin-2(3H)-one |
| I-27 | 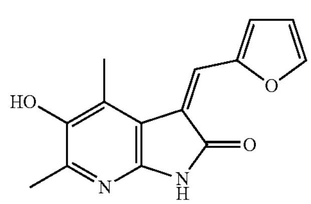 [SMILES: Cc1nc2c(c(C)c1O)/C(=C/c1ccco1)C(=O)N2] | (Z)-3-(Furan-2-ylmethylene)-5-hydroxy-4,6-dimethyl-1H-pyrrolo[2,3-b]pyridin-2(3H)-one |

TABLE 1-continued

| No. | Structure | Chemical Name |
|---|---|---|
| I-28 | 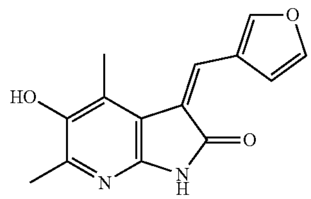 [SMILES: Cc1nc2c(c(C)c1O)/C(=C/c1ccoc1)C(=O)N2] | (Z)-3-(Furan-3-ylmethylene)-5-hydroxy-4,6-dimethyl-1H-pyrrolo[2,3-b]pyridin-2(3H)-one |
| I-29 | 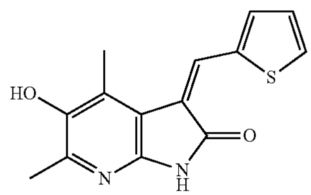 [SMILES: Cc1nc2c(c(C)c1O)/C(=C/c1cccs1)C(=O)N2] | (Z)-5-Hydroxy-4,6-dimethyl-3-(thiophen-2-ylmethylene)-1H-pyrrolo[2,3-b]pyridin-2(3H)-one |
| I-30 | 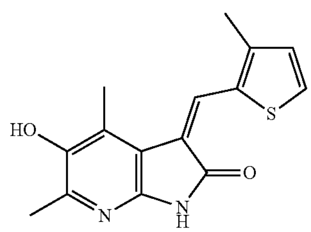 [SMILES: Cc1ccsc1/C=C1\C(=O)Nc2nc(C)c(O)c(C)c21] | (Z)-5-Hydroxy-4,6-dimethyl-3-((3-methylthiophen-2-yl)methylene)-1H-pyrrolo[2,3-b]pyridin-2(3H)-one |
| I-31 | 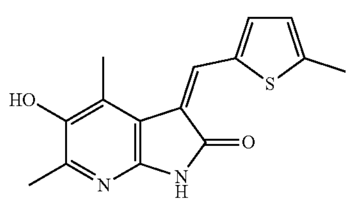 [SMILES: Cc1ccc(/C=C2\C(=O)Nc3nc(C)c(O)c(C)c32)s1] | (Z)-5-Hydroxy-4,6-dimethyl-3-(thiophen-2-ylmethylene)-1H-pyrrolo[2,3-b]pyridin-2(3H)-one |
| I-32 | 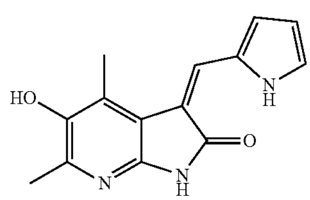 [SMILES: Cc1nc2c(c(C)c1O)/C(=C/c1ccc[nH]1)C(=O)N2] | (Z)-3-((1H-Pyrrol-3-yl)methylene)-5-hydroxy-4,6-dimethyl-1H-pyrrolo[2,3-b]pyridin-2(3H)-one |
| I-33 | 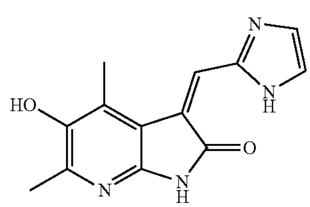 [SMILES: Cc1nc2c(c(C)c1O)/C(=C/c1ncc[nH]1)C(=O)N2] | (Z)-3-((1H-Imidazol-2-yl)methylene)-5-hydroxy-4,6-dimethyl-1H-pyrrolo[2,3-b]pyridin-2(3H)-one |
| I-34 | 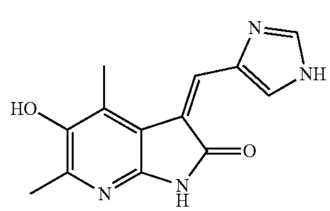 [SMILES: Cc1nc2c(c(C)c1O)/C(=C/c1c[nH]cn1)C(=O)N2] | (Z)-3-((1H-Imidazol-4-yl)methylene)-5-hydroxy-4,6-dimethyl-1H-pyrrolo[2,3-b]pyridin-2(3H)-one |

TABLE 1-continued

| No. | Structure | Chemical Name |
|---|---|---|
| I-35 | 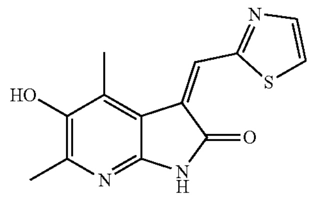 [SMILES: Cc1nc2c(c(C)c1O)/C(=C/c1nccs1)C(=O)N2] | (Z)-5-Hydroxy-4,6-dimethyl-3-(thiazol-2-ylmethylene)-1H-pyrrolo[2,3-b]pyridin-2(3H)-one |
| I-36 | 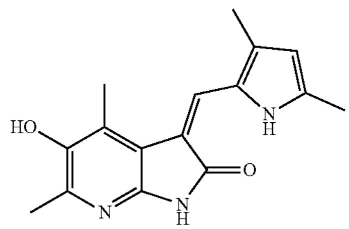 [SMILES: Cc1cc(C)c(/C=C2\C(=O)Nc3nc(C)c(O)c(C)c32)[nH]1] | (Z)-3-((3,5-Dimethyl-1H-pyrrol-2-yl)methylene)-5-hydroxy-4,6-dimethyl-1H-pyrrolo[2,3-b]pyridin-2(3H)-one |
| I-37 | 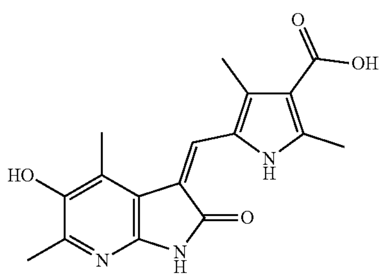 | (Z)-5-((5-Hydroxy-4,6-dimethyl-2-oxo-1H-pyrrolo[2,3-b]pyridin-3(2H)-ylidene)methyl)-2,4-dimethyl-1H-pyrrole-3-carboxylic acid |
| I-38 | 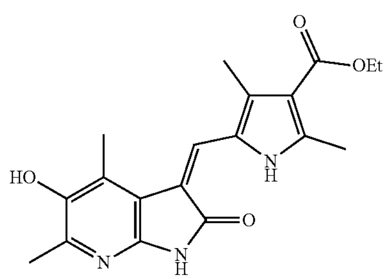 [SMILES: CCOC(=O)c1c(C)[nH]c(/C=C2\C(=O)Nc3nc(C)c(O)c(C)c32)c1C] | (Z)-Ethyl-5-((5-hydroxy-4,6-dimethyl-2-oxo-1H-pyrrolo[2,3-b]pyridin-3(2H)-ylidene)methyl)-2,4-dimethyl-1H-pyrrole-3-carboxylate |
| I-39 | 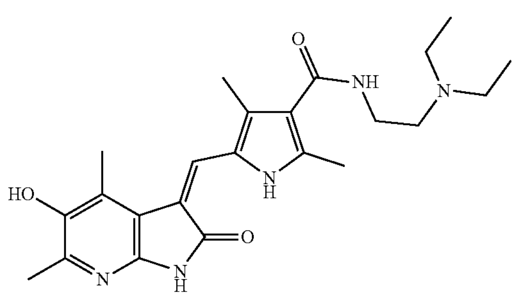 [SMILES: CCN(CC)CCNC(=O)c1c(C)[nH]c(/C=C2\C(=O)Nc3nc(C)c(O)c(C)c32)c1C] | (Z)-N-(2-(Diethylamino)ethyl)-5-((5-hydroxy-4,6-dimethyl-2-oxo-1H-pyrrolo[2,3-b]pyridin-3(2H)-ylidene)methyl)-2,4-dimethyl-1H-pyrrole-3-carboxamide |
| I-40 | 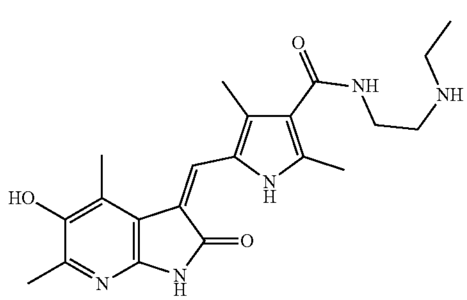 [SMILES: CCNCCNC(=O)c1c(C)[nH]c(/C=C2\C(=O)Nc3nc(C)c(O)c(C)c32)c1C] | (Z)-N-(2-(Ethylamino)ethyl)-5-((5-hydroxy-4,6-dimethyl-2-oxo-1H-pyrrolo[2,3-b]pyridin-3(2H)-ylidene)methyl)-2,4-dimethyl-1H-pyrrole-3-carboxamide |

TABLE 1-continued

| No. | Structure | Chemical Name |
|---|---|---|
| I-41 | 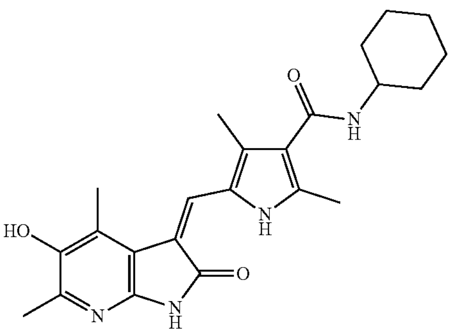 [SMILES: Cc1nc2c(c(C)c1O)/C(=C/c1[nH]c(C)c(C(=O)NC3CCCCC3)c1C)C(=O)N2] | (Z)-N-Cyclohexyl-5-((5-hydroxy-4,6-dimethyl-2-oxo-1H-pyrrolo[2,3-b]pyridin-3(2H)-ylidene)methyl)-2,4-dimethyl-1H-pyrrole-3-carboxamide |
| I-42 | 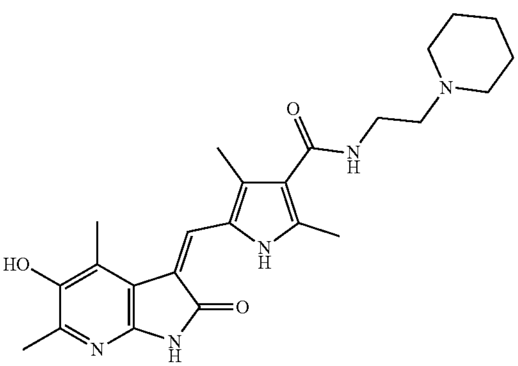 [SMILES: Cc1nc2c(c(C)c1O)/C(=C/c1[nH]c(C)c(C(=O)NCCN3CCCCC3)c1C)C(=O)N2] | (Z)-5-((5-Hydroxy-4,6-dimethyl-2-oxo-1H-pyrrolo[2,3-b]pyridin-3(2H)-ylidene)methyl)-2,4-dimethyl-N-(2-(piperidin-1-yl)ethyl)-1H-pyrrole-3-carboxamide |
| I-43 | 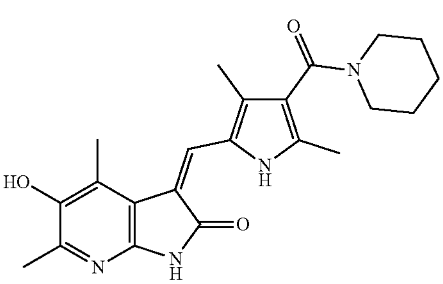 [SMILES: Cc1nc2c(c(C)c1O)/C(=C/c1[nH]c(C)c(C(=O)N3CCCCC3)c1C)C(=O)N2] | (Z)-3-((3,5-Dimethyl-4-(piperidine-1-carbonyl)-1H-pyrrol-2-yl)methylene)-5-hydroxy-4,6-dimethyl-1H-pyrrolo[2,3-b]pyridin-2(3H)-one |
| I-44 | 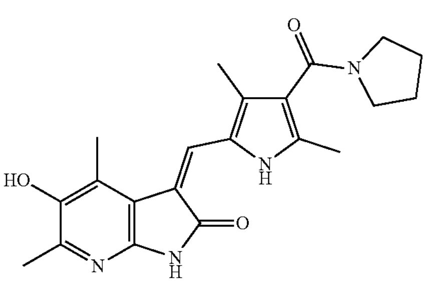 [SMILES: Cc1nc2c(c(C)c1O)/C(=C/c1[nH]c(C)c(C(=O)N3CCCC3)c1C)C(=O)N2] | (Z)-3-((3,5-Dimethyl-4-(pyrrolidine-1-carbonyl)-1H-pyrrol-2-yl)methylene)-5-hydroxy-4,6-dimethyl-1H-pyrrolo[2,3-b]pyridin-2(3H)-one |
| I-45 | 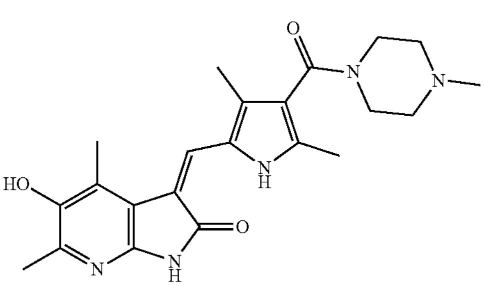 [SMILES: Cc1nc2c(c(C)c1O)/C(=C/c1[nH]c(C)c(C(=O)N3CCN(C)CC3)c1C)C(=O)N2] | (Z)-3-((3,5-Dimethyl-4-(4-methylpiperazine-1-carbonyl)-1H-pyrrol-2-yl)methylene)-5-hydroxy-4,6-dimethyl-1H-pyrrolo[2,3-b]pyridin-2(3H)-one |

TABLE 1-continued

| No. | Structure | Chemical Name |
|---|---|---|
| I-46 | 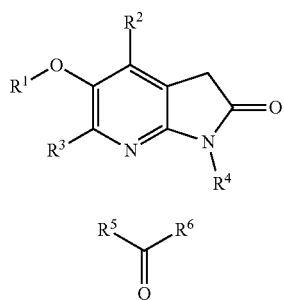 | (Z)-3-((3,5-Dimethyl-4-(morpholine-4-carbonyl)-1H-pyrrol-2-yl)methylene)-5-hydroxy-4,6-dimethyl-1H-pyrrolo[2,3-b]pyridin-2(3H)-one |

In the present invention, the pharmaceutically acceptable salt may be in the form of acid addition salts that are formed by an organic acid selected from the group consisting of oxalic acid, maleic acid, fumaric acid, malic acid, tartaric acid, citric acid and benzoic acid, or an inorganic acid selected from the group consisting of hydrochloric acid, sulfuric acid, phosphoric acid and hydrobromic acid.

In addition, the present invention provides a method for preparing the compound of Formula 1. The compound of Formula 1 may be prepared, for example, by reacting a compound of the following Formula 2 with a compound of the following Formula 3:

[Formula 2]

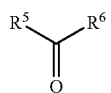

[Formula 3]

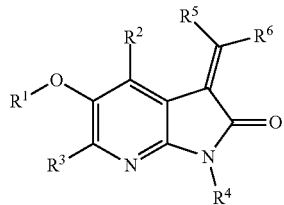

[Formula 1]

wherein, $R^1$, $R^4$ and $R^5$ each independently represent any one selected from the group consisting of hydrogen; halogen; and $C_1$-$C_4$ alkyl;

$R^2$ and $R^3$ each independently represent $C_1$-$C_4$ alkyl;

$R^6$ represents any one selected from the group consisting of hydrogen; $C_1$-$C_{12}$ alkyl; $C_2$-$C_{12}$ alkenyl; $C_6$-$C_{12}$ aryl; and $C_3$-$C_{12}$ heteroaryl containing 1 to 3 heteroatoms;

wherein the $C_1$-$C_{12}$ alkyl or the $C_2$-$C_{12}$ alkenyl is unsubstituted or substituted with $C_6$-$C_{12}$ aryl;

the $C_6$-$C_{12}$ aryl is unsubstituted or substituted with one or more substituents selected from the group consisting of halogen; —$NO_2$; $C_1$-$C_4$ alkyl; —$OR^{11}$; and —$NR^{20}R^{21}$;

the $C_3$-$C_{12}$ heteroaryl is unsubstituted or substituted with one or more substituents selected from the group consisting of $C_1$-$C_4$ alkyl; —$C(O)R^{14}$; —$C(O)OR^{15}$; and —$C(O)NR^{22}R^{23}$;

$R^{11}$, $R^{14}$ and $R^{15}$ each independently represent any one selected from the group consisting of hydrogen; and $C_1$-$C_4$ alkyl;

$R^{20}$ to $R^{23}$ each independently represent any one selected from the group consisting of hydrogen; and $C_1$-$C_6$ alkyl, or $R^{22}$ and $R^{23}$ taken together may form $C_3$-$C_8$ heteroaryl containing 1 to 3 heteroatoms;

wherein the $C_1$-$C_4$ alkyl and the $C_3$-$C_8$ heteroaryl of $R^{11}$, $R^{14}$, $R^{15}$, and $R^{20}$ to $R^{23}$ are each independently unsubstituted or substituted with one or more substituents selected from the group consisting of $C_1$-$C_4$ alkyl; and —$NR^{24}R^{25}$;

$R^{24}$ and $R^{25}$ each independently represent any one selected from the group consisting of hydrogen; and $C_1$-$C_4$ alkyl, or $R^{24}$ and $R^{25}$ taken together may form $C_3$-$C_8$ heteroaryl containing 1 to 3 heteroatoms.

In one embodiment, the compound of Formula 1 may be prepared by a method such as Reaction Scheme 1 below:

[Reaction Scheme 1]

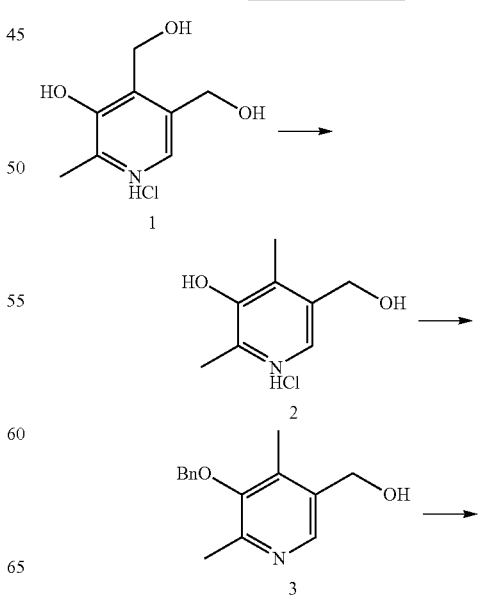

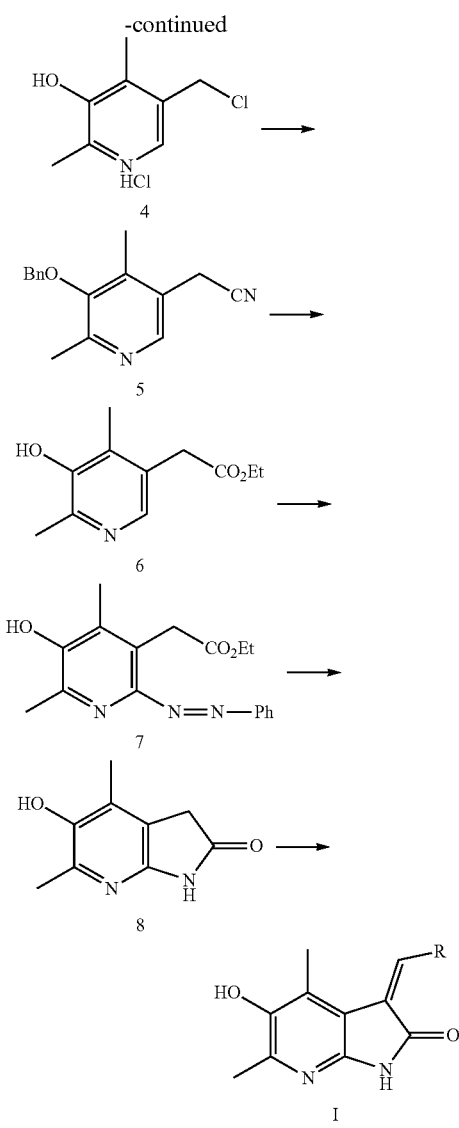

Reaction Formula 1 may be processed according to Examples 1 to 7.

In addition, the present invention provides a pharmaceutical composition for the prevention or treatment of cancer disease, comprising the above-mentioned compound of Formula 1 or a pharmaceutically acceptable salt thereof as an active ingredient.

In addition, the present invention provides a pharmaceutical composition for the prevention or inhibition of cancer invasion or cancer metastasis, comprising the above-mentioned compound of Formula 1 or a pharmaceutically acceptable salt thereof as an active ingredient.

The cancer may be any one selected from the group consisting of lung cancer, breast cancer, bladder cancer, bone cancer, thyroid cancer, parathyroid cancer, rectal cancer, prostate cancer, renal cancer, laryngopharyngeal cancer, larynx cancer, esophageal cancer, pancreatic cancer, colorectal cancer, stomach cancer, tongue cancer, skin cancer, brain tumor, uterine cancer, head or neck cancer, gallbladder cancer, oral cancer, colon cancer, anal cancer, tumors of the central nervous system and liver cancer.

The compound of Formula 1 according to the present invention or a pharmaceutically acceptable salt thereof can be administered as such to a patient or can be administered in pharmaceutical compositions in which the compounds are mixed with a suitable carrier or excipient. Techniques for formulation and administration of drugs may be found in "Remington's Pharmacological Sciences," Mack Publishing Co., Easton, Pa., latest edition.

According to the above document, the term "administration" or "administer" refers to the delivery of the compound of Formula 1 or a pharmaceutically acceptable salt thereof, or a pharmaceutical composition comprising the compound of Formula 1 to an organism for the treatment or prevention of the aforementioned diseases.

Suitable routes of administration may be oral, rectal, transmucosal or intestinal administration or intramuscular, subcutaneous, intramedullary, intrathecal, direct intraventricular, intravascular, intravitreal, intraperitoneal, intranasal, or intraocular injections. The preferred routes of administration may be oral and parenteral.

Alternatively, the compound may be administered by topical (local) administration rather than by systemic administration, for example, via a direct injection of the compound into a solid tumor, often in a depot formulation or a sustained release formulation.

Furthermore, the drug can be administered in a targeted drug delivery system, for example, in a liposome coated with a tumor-specific antibody. The liposomes may target the tumor and be taken up selectively by the tumor.

The pharmaceutical composition of the present invention may be manufactured by processes well known in the art, e.g., by means of conventional mixing, dissolving, granulating, dragee-making, levigating, emulsifying, encapsulating, entrapping and lyophilizing processes.

The pharmaceutical compositions according to the present invention may be formulated with the active compound into preparations which can be used pharmaceutically. A proper formulation may vary depending on the selection of the route of administration.

For injection, the compound of the present invention may be formulated in aqueous solutions, preferably in physiologically compatible buffers such as Hanks' solution, Ringer's solution, or physiological saline buffer.

For nasal transmucosal administration, penetrants that allow the drug to penetrate the barrier may be used in the formulation. Penetrants generally known in the art may be used.

For oral administration, the compound can be formulated by combining with pharmaceutically acceptable carriers. Such carriers enable the compound of the present invention to be formulated as tablets, pills, lozenges, dragees, capsules, liquids, gels, syrups, slurries, suspensions and the like, for oral ingestion by a patient. Pharmaceutical preparations for oral use can be made using a solid excipient, after adding other suitable auxiliaries if desired, to obtain a core of tablets or dragees. Optionally, the resulting mixture may be ground and processed for preparing granules. Useful excipients may be sugars including lactose, sucrose, mannitol, or sorbitol, cellulose preparations such as maize starch, wheat starch, rice starch and potato starch, and fillers such as gelatin, gums, rubber sap, methyl cellulose, hydroxypropylmethylcellulose and/or polyvinyl-pyrrolidone (PVP). If desired, disintegrating agents such as cross-linked polyvinyl pyrrolidone, agar, or alginic acid may be added. A salt such as sodium alginate may also be added.

Dragee cores may be prepared by suitable coating. For this purpose, concentrated sugar solutions may be used that may optionally contain gum arabic, polyvinyl pyrrolidone, carbopol gel, polyethylene glycol and/or titanium dioxide, lacquer solutions.

Pharmaceutical compositions that can be used orally include push-fit capsules made of gelatin, as well as soft, sealed capsules made of gelatin and a plasticizer, such as glycerol or sorbitol. In soft capsules, the active compound may be dissolved or suspended in suitable liquids, such as fatty oils, liquid paraffin, or liquid polyethylene glycols. Stabilizers may also be added in the composition.

Pharmaceutical compositions that may be used include hard gelatin capsules.

The capsules may be packaged into brown glass or plastic bottles to protect the active compound from light. The containers containing the active compound capsule formulation may be stored at controlled room temperature (15-30° C.).

For administration by inhalation, the compound according to the present invention may be conveniently delivered in the form of an aerosol spray using a compression container, a nebulizer and a suitable propellant, e.g., dichlorodifluoromethane, trichlorofluoromethane, dichlorotetra-fluoroethane and carbon dioxide.

The compound may also be formulated for parenteral administration, e.g., by bolus injection or continuous intravenous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water-soluble form, for example, aqueous solutions of a water-soluble form of the active compound, such as a salt. Additionally, suspensions of the active compound may be prepared in a lipophilic vehicle. Suitable lipophilic vehicles include fatty oils, synthetic fatty acid esters such as ethyl oleate and triglycerides, and materials such as liposomes. Aqueous injection suspensions may contain substances which increase the viscosity of the suspension, such as sodium carboxy methyl cellulose, sorbitol or dextran. Optionally, the suspension may also contain suitable stabilizers and/or agents that increase the solubility of the compound to allow for the preparation of highly concentrated solutions.

The compound may also be formulated in suppositories using conventional suppository bases such as cocoa butter or other glycerides, or in rectal compositions such as retention enemas.

In addition to the formulations described previously, the compound may also be formulated as a depot preparation. Such long-acting formulations may be administered by implantation (for example, subcutaneously or intramuscularly) or by intramuscular injection. A compound of the present invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

The pharmaceutical composition according to the present invention means a composition containing an active compound in an amount sufficient to achieve the intended purpose, e.g., prevention or treatment of a disease selected from the group consisting of lung cancer, breast cancer, bladder cancer, bone cancer, thyroid cancer, parathyroid cancer, rectal cancer, prostate cancer, renal cancer, laryngopharyngeal cancer, larynx cancer, esophageal cancer, pancreatic cancer, colorectal cancer, stomach cancer, tongue cancer, skin cancer, brain tumor, uterine cancer, head or neck cancer, gallbladder cancer, oral cancer, colon cancer, anal cancer, tumors of the central nervous system, liver cancer and colorectal cancer.

In this case, a therapeutically effective amount means an amount effective to prevent, alleviate or ameliorate symptoms of disease or prolong the survival of the subject being treated.

The pharmaceutical composition according to the present invention may contain the compound of Formula 1 or a pharmaceutically acceptable salt thereof in an amount of 0.1 to 50 wt % based on total weight of the composition.

The compound of Formula 1 according to the present invention or a pharmaceutically acceptable salt thereof may be used in an amount of 0.01 to 100 mg/kg, and preferably 0.1 to 10 mg/kg once or several times a day, but the amount may be changed depending on the age, sex and body weight of the patient. The amount for administration of the compound of Formula 1 or a pharmaceutically acceptable salt thereof may increase or decrease depending on the administration route, severity of the disease, sex, body weight and age, etc. Therefore, the above-mentioned amounts for administration do not limit the scope of the present invention.

The pharmaceutical composition may be administered into mammals such as rats, mice, livestock and humans via various routes.

The 50% lethal dose ($LD_{50}$) of the compound of Formula 1 according to the present invention or a pharmaceutically acceptable salt thereof is at least 2 g/kg. That is, the compound of Formula 1 or a pharmaceutically acceptable salt thereof is sufficiently safe and can be used for the pharmaceutical composition of the present invention.

In addition, the compound of Formula 1 of the present invention or a pharmaceutically acceptable salt or prodrug thereof may be combined with other chemotherapeutic agents for treating the above-mentioned conditions and diseases. The other chemotherapeutic agents may be medicines for treating lung cancer, breast cancer, bladder cancer, bone cancer, thyroid cancer, parathyroid cancer, rectal cancer, prostate cancer, renal cancer, laryngopharyngeal cancer, larynx cancer, esophageal cancer, pancreatic cancer, colorectal cancer, stomach cancer, tongue cancer, skin cancer, brain tumor, uterine cancer, head or neck cancer, gallbladder cancer, oral cancer, colon cancer, anal cancer, tumors of the central nervous system, liver cancer and/or colorectal cancer.

Modes for Carrying Out the Invention

Examples

<Example 1> Preparation of 5-(Hydroxymethyl)-2,4-dimethylpyridin-3-ol hydrochloride (2)

After adding Zinc (Zn) powder (12.7 g, 0.195 mol) in small portions to a solution of pyridoxine hydrochloride (1, 10.0 g, 48.6 mmol) in acetic acid (40 mL), the mixture was refluxed for 24 hours. After cooling the reaction mixture to room temperature, the reaction mixture was filtered under reduced pressure and washed with acetonitrile ($CH_3CN$, 50 mL), and an excess amount of hydrochloric acid-methanol solution (150 mL) was added to the filtrate. After stirring for 2 hours under ice-cooling, the resulting suspension was filtered under reduced pressure to obtain the desired compound 2 (8.7 g, 94%) as a white solid.

$^1$H-NMR ((CD$_3$)$_2$SO) δ 10.62 (br s, 1H), 8.08 (s, 1H), 5.70 (br s, 1H), 4.60 (s, 2H), 2.61 (s, 3H), 2.32 (s, 3H).

<Example 2> Preparation of (5-(Benzyloxy)-4,6-dimethylpyridin-3-yl)methanol (3)

After adding potassium carbonate (107 g, 0.776 mol) and benzyl chloride (26.2 mL, 0.228 mol) to a solution of compound 2 (8.6 g, 45.7 mmol) in DMF (N, N-dimethylformamide, 450 mL), the mixture was stirred at room temperature for 24 hours. After concentrating the reaction solution under reduced pressure, the reaction solution was diluted with ethyl acetate (EtOAc, 1 L) and washed with water (3×100 mL). The ethyl acetate solution was washed with saturated brine, dried and filtered using anhydrous magnesium sulfate (MgSO$_4$), and concentrated under reduced pressure. The residue was purified by column chromatography (CH$_2$Cl$_2$:MeOH=20:1) to obtain the desired compound 3 (8.2 g, 74%) as a brown solid.

$^1$H-NMR (CDCl$_3$) δ 8.07 (s, 1H), 7.38-7.47 (m, 5H), 4.80 (s, 2H), 4.65 (s, 2H), 2.48 (s, 3H), 2.32 (s, 3H).

<Example 3> Preparation of 3-Benzyloxy-5-chloromethyl-2,4-dimethylpyridine hydrochloride (4)

DMF (0.09 mL, 23.43 mmol) and thionyl chloride (1.7 mL, 23.43 mmol) were added to a solution of compound 3 (2.85 g, 11.71 mmol) in 1,2-dichloroethane (35 mL), and the mixture was stirred for 1 hour at 80° C. After cooling the reaction solution to room temperature, ethyl ether (150 mL) was added to the reaction solution, which was stirred for 1 hour under ice-cooling. After filtering the precipitated solid off under reduced pressure, the filtered solid was washed with ethyl ether and dried to obtain the desired compound 4 (3 g, 86%) as a brown solid.

$^1$H-NMR (CDCl$_3$) δ 8.19 (s, 1H), 7.34-7.44 (m, 5H), 4.81 (s, 2H), 4.56 (s, 2H), 2.50 (s, 3H), 2.32 (s, 3H).

<Example 4> Preparation of 2-(5-Benzyloxy-4,6-dimethylpyridin-3-yl)acetonitrile (5)

Potassium cyanide (KCN, 7.42 g, 114.04 mmol) was added to a solution of compound 4 (9.95 g, 38.01 mmol) in DMF (500 mL), and the mixture was stirred at 30-40° C. for 2 days. After concentrating the reaction solution, the residue was diluted with ethyl acetate (2 L) and washed with water (4×200 mL). The ethyl acetate solution was dried and filtered using anhydrous magnesium sulfate, and concentrated under reduced pressure. The residue was purified by column chromatography (CHCl$_3$:MeOH=50:1→20:1) to obtain the desired compound 5 (8.06 g, 95%) as a brown solid.

$^1$H-NMR (CDCl$_3$) δ 8.18 (s, 1H), 7.35-7.43 (m, 5H), 4.80 (s, 2H), 3.61 (s, 2H), 2.51 (s, 3H), 2.26 (s, 3H).

<Example 5> Preparation of Ethyl 2-(5-hydroxy-4,6-dimethylpyridin-3-yl)acetate (6)

Concentrated sulfuric acid (3.7 mL, 69.36 mmol) was added to a solution of compound 5 (500 mg, 1.98 mmol) in ethanol (20 mL), and the mixture was refluxed for 24 hours. The reaction solution was cooled to room temperature and diluted with ethanol (150 mL). Sodium carbonate (Na$_2$CO$_3$, 7.35 g, 69.36 mmol) was added to the reaction solution in small portions, and the mixture was stirred at room temperature for 3 hours. The reaction solution was concentrated, and the residue was diluted with ethyl acetate (150 mL), filtered under reduced pressure to filter out solids and washed with ethyl acetate. After concentrating the filtrate under reduced pressure, the residue was purified by column chromatography (CHCl$_3$:MeOH=70:1→20:1) to obtain the desired compound 6 (366 mg, 88%) as a yellow solid.

$^1$H-NMR (CDCl$_3$) δ 7.80 (s, 1H), 6.96 (br s, 1H), 4.11 (q, J=7.1 Hz, 2H), 3.56 (s, 2H), 2.38 (s, 3H), 2.19 (s, 3H), 1.21 (t, J=7.1 Hz, 3H).

<Example 6> Preparation of Ethyl 2-(5-hydroxy-4,6-dimethyl-2-(phenyldiazenyl)pyridin-3-yl)acetate (7)

Compound 6 (1 g, 4.78 mmol) was dissolved in a mixed solvent of water-THF (tetrahydrofuran) (1:1, 30 mL) in a beaker, and the mixture was stirred and cooled under ice-cooling with a stirrer and a pH meter. After dissolving aniline (0.48 mL, 5.26 mmol) in 6M-hydrochloric acid (5 mL) in a separate Erlenmeyer flask, the mixture was cooled under ice-cooling. Then, a cold solution of NaNO$_2$ (sodium nitrite, 363 mg, 5.26 mmol) in water (2 mL) was added to the aniline-hydrochloric acid solution in small portions to prepare a diazotized aniline solution. This diazotized aniline solution was added in small portions to a cold solution of compound 6. At the same time, the reaction solution was maintained at pH 8 with a 10M-sodium hydroxide solution. All of the diazotized aniline solution was added thereto, and the reaction solution was stirred at room temperature for 2 hours. The reaction solution was extracted with ethyl acetate (3×150 mL), and the ethyl acetate solution was washed with saturated brine, dried and filtered using anhydrous magnesium sulfate, and concentrated under reduced pressure. The residue was purified by column chromatography (CHCl$_3$:MeOH=80:1→20:1) to obtain the desired compound 7 (1.3 g, 87%) as a red solid.

$^1$H-NMR (CDCl$_3$) δ 7.32-7.37 (m, 4H), 7.08-7.13 (m, 1H), 4.14 (q, J=7.1 Hz, 2H), 3.89 (s, 2H), 2.40 (s, 3H), 2.06 (s, 3H), 1.22 (t, J=7.1 Hz, 3H).

<Example 7> Preparation of 5-Hydroxy-4,6-dimethyl-1H-pyrrolo[2,3-b]pyridin-2(3H)-one (8)

Zinc (Zn) powder (344 mg, 5.26 mmol) was added in small portions to a solution of compound 7 (550 mg, 1.75 mmol) in acetic acid (35 mL), and the mixture was refluxed for 12 hours. After cooling the reaction solution to room temperature, the reaction solution was filtered under reduced pressure to filter out solids, and washed with acetonitrile (CH$_3$CN). After concentrating the filtrate, the residue was purified by column chromatography (CHCl$_3$:MeOH=80:1→10:1) to obtain the desired compound 8 (273 mg, 87%) as a brown solid.

$^1$H-NMR ((CD$_3$)$_2$SO) δ 10.4 (s, 1H), 8.05 (s, 1H), 3.38 (s, 2H), 2.27 (s, 3H), 2.07 (s, 3H).

<Example 8-1> Preparation of (Z)-3-Hexylidene-5-hydroxy-4,6-dimethyl-1H-pyrrolo[2,3-b]pyridin-2(3H)-one (I-01)

1-hexanal (20.7 μL, 0.168 mmol) and piperidine (22.3 μL, 0.224 mmol) were added to a solution of compound 8 (20 mg, 0.112 mmol) in methanol (1 mL), and the mixture was stirred at room temperature for 2 hours. The solid in the reaction solution was filtered under reduced pressure, and the filtered solid was washed with ethyl acetate and dried to obtain the desired compound 1-01 (26 mg, 88%) as a yellow solid.

$^1$H-NMR ((CD$_3$)$_2$SO) δ 10.59 (s, 1H), 8.12 (s, 1H), 6.90 (t, J=7.7 Hz, 1H), 2.93 (q, J=7.5 Hz, 2H), 2.30 (s, 6H), 1.52-1.48 (m, 2H), 1.35-1.31 (m, 4H), 0.88 (t, J=6.9 Hz, 3H).

Examples 8-2 to 8-46

The desired compounds of Examples 8-2 to 8-46 were prepared in the same manner as in Example 8-1 except the compounds corresponding to the desired compounds were used instead of 1-hexanal and piperidine used in Example 8-1.

<Example 8-2> Preparation of (Z)-3-(2-Ethylbutylidene)-5-hydroxy-4,6-dimethyl-1H-pyrrolo[2,3-b]pyridin-2(3H)-one (I-02)

$^1$H-NMR ((CD$_3$)$_2$SO) δ 11.07 (s, 1H), 6.71 (d, J=10.4 Hz, 1H), 3.82 (s, 1H), 2.35 (d, J=1.6 Hz, 6H), 1.62-1.49 (m, 2H), 1.42-1.29 (m, 2H), 0.83 (t, J=7.3 Hz, 6H).

<Example 8-3> Preparation of (Z)-5-Hydroxy-4,6-dimethyl-3-(3-methylbut-2-enylidene)-1H-pyrrolo[2,3-b]pyridin-2(3H)-one (I-03)

$^1$H-NMR (CD$_3$OD) δ 7.86 (d, J=12.1 Hz, 1H), 7.70 (d, J=11.9 Hz, 1H), 2.63 (s, 3H), 2.53 (s, 3H), 2.07 (s, 6H).

<Example 8-4> Preparation of (Z)-5-Hydroxy-3-((E)-3-(4-hydroxy-3-methoxyphenyl)allylidene)-4,6-dimethyl-1H-pyrrolo[2,3-b]pyridin-2(3H)-one (I-04)

$^1$H-NMR ((CD$_3$)$_2$SO) δ 11.05 (s, 1H), 8.36 (dd, J=15.5, 11.4 Hz, 1H), 7.53 (d, J=11.5 Hz, 1H), 7.23 (d, J=15.5 Hz, 1H), 7.07 (d, J=9.4 Hz, 2H), 6.85 (d, J=8.0 Hz, 1H), 3.82 (s, 3H), 2.43 (s, 3H), 2.34 (s, 3H).

<Example 8-5> Preparation of (Z)-3-(Cyclohexylmethylene)-5-hydroxy-4,6-dimethyl-1H-pyrrolo[2,3-b]pyridin-2(3H)-one (I-05)

$^1$H-NMR (CD$_3$OD) δ 6.80 (d, J=9.8 Hz, 1H), 3.83 (d, J=10.1 Hz, 1H), 2.38 (d, J=1.8 Hz, 6H), 1.80 (d, J=11.4 Hz, 4H), 1.34 (dt, J=20.7, 11.4 Hz, 6H).

<Example 8-6> Preparation of (Z)-5-Hydroxy-4,6-dimethyl-3-(4-methylbenzylidene)-1H-pyrrolo[2,3-b]pyridin-2(3H)-one (I-06)

$^1$H-NMR (CD$_3$OD) δ 8.09 (d, J=8.1 Hz, 2H), 7.97 (s, 1H), 7.26 (d, J=8.0 Hz, 2H), 2.71 (s, 3H), 2.56 (s, 3H), 2.40 (s, 3H).

<Example 8-7> Preparation of (Z)-5-Hydroxy-4,6-dimethyl-3-(2-nitrobenzylidene)-1H-pyrrolo[2,3-b]pyridin-2(3H)-one (I-07)

$^1$H-NMR (CD$_3$OD) δ 8.40 (s, 1H), 8.26 (d, J=8.0 Hz, 1H), 8.26 (d, J=8.0 Hz, 1H), 7.78-7.62 (m, 4H), 2.69 (s, 3H), 2.57 (s, 3H).

<Example 8-8> Preparation of (Z)-5-Hydroxy-4,6-dimethyl-3-(4-nitrobenzylidene)-1H-pyrrolo[2,3-b]pyridin-2(3H)-one (I-08)

$^1$H-NMR (CD$_3$OD) δ 8.28 (s, 1H), 8.24 (s, 1H), 8.18 (s, 1H), 8.15 (s, 1H), 8.11 (s, 1H), 2.74 (s, 3H), 2.60 (s, 3H).

<Example 8-9> Preparation of (Z)-3-(4-Fluorobenzylidene)-5-hydroxy-4,6-dimethyl-1H-pyrrolo[2,3-b]pyridin-2(3H)-one (I-09)

$^1$H-NMR (CD$_3$OD) δ 8.31-8.20 (m, 2H), 8.03 (s, 1H), 7.24-7.14 (m, 2H), 2.73 (s, 3H), 2.57 (s, 3H).

<Example 8-10> Preparation of (Z)-3-(4-Chlorobenzylidene)-5-hydroxy-4,6-dimethyl-1H-pyrrolo[2,3-b]pyridin-2(3H)-one (I-10)

$^1$H-NMR ((CD$_3$)$_2$SO) δ 11.27 (s, 1H), 8.11 (d, J=8.5 Hz, 2H), 7.74 (s, 1H), 7.47 (d, J=8.5 Hz, 2H), 2.52 (s, 3H), 2.40 (s, 3H).

<Example 8-11> Preparation of (Z)-5-Hydroxy-3-(2-hydroxybenzylidene)-4,6-dimethyl-1H-pyrrolo[2,3-b]pyridin-2(3H)-one (I-11)

$^1$H-NMR ((CD$_3$)$_2$SO) δ 11.06 (s, 1H), 10.55-10.04 (m, 1H), 8.31 (d, J=7.7 Hz, 1H), 7.98 (s, 1H), 7.25 (t, J=7.6 Hz, 1H), 6.95 (d, J=8.2 Hz, 1H), 6.80 (t, J=7.5 Hz, 1H), 2.45 (s, 3H), 2.37 (s, 3H).

<Example 8-12> Preparation of (Z)-5-hydroxy-3-(2-methoxybenzylidene)-4,6-dimethyl-1H-pyrrolo[2,3-b]pyridin-2(3H)-one (I-12)

$^1$H-NMR ((CD$_3$)$_2$SO) δ 10.80 (s, 1H), 8.16 (d, J=7.8 Hz, 1H), 7.86 (s, 1H), 7.40 (t, J=7.8 Hz, 1H), 7.06 (d, J=8.4 Hz, 1H), 6.94 (t, J=7.6 Hz, 1H), 3.86 (s, 3H), 2.42 (s, 3H), 2.35 (s, 3H).

<Example 8-13> Preparation of (Z)-5-Hydroxy-3-(3-methoxybenzylidene)-4,6-dimethyl-1H-pyrrolo[2,3-b]pyridin-2(3H)-one (I-13)

$^1$H-NMR ((CD$_3$)$_2$SO) δ 11.21 (s, 1H), 7.91 (s, 1H), 7.75 (s, 1H), 7.63 (d, J=7.7 Hz, 1H), 7.35 (t, J=8.0 Hz, 1H), 7.01 (dd, J=8.2, 2.5 Hz, 1H), 3.80 (s, 3H), 2.53 (s, 3H), 2.40 (s, 3H).

<Example 8-14> Preparation of (Z)-5-Hydroxy-3-(4-methoxybenzylidene)-4,6-dimethyl-1H-pyrrolo[2,3-b]pyridin-2(3H)-one (I-14)

$^1$H-NMR (CD$_3$OD) δ 8.32 (d, J=8.9 Hz, 2H), 7.99 (s, 1H), 7.02 (t, J=6.1 Hz, 2H), 3.89 (d, J=3.0 Hz, 3H), 2.73 (s, 3H), 2.56 (s, 3H).

<Example 8-15> Preparation of (Z)-3-(2,5-Dimethoxybenzylidene)-5-hydroxy-4,6-dimethyl-1H-pyrrolo[2,3-b]pyridin-2(3H)-one (I-15)

$^1$H-NMR (CD$_3$OD) δ 8.35 (s, 1H), 8.16 (d, J=2.9 Hz, 1H), 7.13-6.94 (m, 2H), 3.91-3.87 (m, 3H), 3.82-3.77 (m, 3H), 2.69-2.60 (m, 3H), 2.56-2.51 (m, 3H).

<Example 8-16> Preparation of (Z)-5-Hydroxy-4,6-dimethyl-3-(3,4,5-trimethoxybenzylidene)-1H-pyrrolo[2,3-b]pyridin-2(3H)-one (I-16)

$^1$H-NMR ((CD$_3$)$_2$SO) δ 11.20 (s, 1H), 7.76 (s, 2H), 7.72 (s, 1H), 3.82 (s, 6H), 3.74 (s, 3H), 2.54 (s, 3H), 2.39 (s, 3H).

<Example 8-17> Preparation of (Z)-3-(5-bromo-2-methoxybenzylidene)-5-hydroxy-4,6-dimethyl-1H-pyrrolo[2,3-b]pyridin-2(3H)-one (I-17)

$^1$H-NMR (CD$_3$OD) δ 8.45 (d, J=2.4 Hz, 1H), 8.19 (s, 1H), 7.58 (dd, J=8.9, 2.5 Hz, 1H), 7.03 (d, J=8.9 Hz, 1H), 3.93 (s, 3H), 2.68 (s, 3H), 2.57 (s, 3H).

<Example 8-18> Preparation of (Z)-3-(4-(Dimethylamino)benzylidene)-5-hydroxy-4,6-dimethyl-1H-pyrrolo[2,3-b]pyridin-2(3H)-one (I-18)

$^1$H-NMR ((CD$_3$)$_2$SO) δ 10.45 (s, 1H), 8.28 (d, J=9.0 Hz, 2H), 7.94 (br s, 1H), 7.56 (s, 1H), 6.74 (d, J=9.0 Hz, 2H), 3.03 (s, 6H), 2.47 (s, 3H), 2.33 (s, 3H).

<Example 8-19> Preparation of (Z)-3-(2,2-Diphenylethylidene)-5-hydroxy-4,6-dimethyl-1H-pyrrolo[2,3-b]pyridin-2(3H)-one (I-19)

$^1$H-NMR (CD$_3$OD) δ 7.72 (d, J=10.8 Hz, 1H), 7.35-7.24 (m, 11H), 6.78 (d, J=10.7 Hz, 1H), 2.61 (s, 3H), 2.55 (s, 3H).

<Example 8-20> Preparation of (Z)-5-Hydroxy-4,6-dimethyl-3-(naphthalen-2-ylmethylene)-1H-pyrrolo[2,3-b]pyridin-2(3H)-one (I-20)

$^1$H-NMR ((CD$_3$)$_2$SO) δ 11.33 (s, 1H), 8.59 (s, 1H), 8.28 (d, J=8.5 Hz, 1H), 7.99-7.83 (m, 4H), 7.56 (s, 2H), 2.56 (s, 3H), 2.40 (s, 3H).

<Example 8-21> Preparation of (Z)-5-Hydroxy-4,6-dimethyl-3-(pyridin-2-ylmethylene)-1H-pyrrolo[2,3-b]pyridin-2(3H)-one (I-21)

$^1$H-NMR (CD$_3$OD) δ 9.07 (dd, J=5.8, 1.3 Hz, 1H), 8.75 (td, J=7.9, 1.6 Hz, 1H), 8.56 (d, J=8.1 Hz, 1H), 8.22-8.14 (m, 1H), 8.05 (s, 1H), 2.77 (s, 3H), 2.58 (s, 3H).

<Example 8-22> Preparation of (Z)-5-Hydroxy-4,6-dimethyl-3-(pyridin-3-ylmethylene)-1H-pyrrolo[2,3-b]pyridin-2(3H)-one (I-22)

$^1$H-NMR (CD$_3$OD) δ 9.45 (s, 1H), 9.02 (d, J=8.2 Hz, 1H), 8.86 (d, J=5.8 Hz, 1H), 8.16 (dd, J=8.0, 5.9 Hz, 1H), 8.07 (s, 1H), 2.73 (s, 3H), 2.57 (s, 3H).

<Example 8-23> Preparation of (Z)-5-Hydroxy-4,6-dimethyl-3-(pyridin-4-ylmethylene)-1H-pyrrolo[2,3-b]pyridin-2(3H)-one (I-23)

$^1$H-NMR (CD$_3$OD) δ 8.83 (d, J=6.8 Hz, 2H), 8.41 (d, J=6.3 Hz, 2H), 7.87 (s, 1H), 2.59 (s, 3H), 2.46 (s, 3H).

<Example 8-24> Preparation of (Z)-5-Hydroxy-4,6-dimethyl-3-(quinolin-2-ylmethylene)-1H-pyrrolo[2,3-b]pyridin-2(3H)-one (I-24)

$^1$H-NMR (CD$_3$OD) δ 9.27 (d, J=8.6 Hz, 1H), 8.53 (d, J=8.6 Hz, 1H), 8.43-8.20 (m, 5H), 8.06 (dd, J=11.1, 4.1 Hz, 1H), 2.83 (s, 3H), 2.61 (s, 3H).

<Example 8-25> Preparation of (Z)-3-((1H-Indol-4-yl)methylene)-5-hydroxy-4,6-dimethyl-1H-pyrrolo[2,3-b]pyridin-2(3H)-one (I-25)

$^1$H-NMR ((CD$_3$)$_2$SO) δ 11.38 (s, 1H), 10.99 (s, 1H), 8.39 (d, J=7.5 Hz, 1H), 8.12 (s, 1H), 7.51 (d, J=8.3 Hz, 2H), 7.15 (t, J=7.8 Hz, 1H), 6.67 (s, 1H), 2.59 (s, 3H), 2.39 (s, 3H).

<Example 8-26> Preparation of (Z)-3-((1H-Indol-3-yl)methylene)-5-hydroxy-4,6-dimethyl-1H-pyrrolo[2,3-b]pyridin-2(3H)-one (I-26)

$^1$H-NMR ((CD$_3$)$_2$SO) δ 12.40 (d, J=2.4 Hz, 1H), 11.64 (s, 1H), 9.37 (d, J=3.0 Hz, 1H), 8.15 (s, 1H), 7.91 (dd, J=6.4, 2.6 Hz, 1H), 7.54 (dd, J=6.2, 2.8 Hz, 1H), 7.29-7.23 (m, 2H), 2.69 (s, 3H), 2.44 (s, 3H).

<Example 8-27> Preparation of (Z)-3-(Furan-2-ylmethylene)-5-hydroxy-4,6-dimethyl-1H-pyrrolo[2,3-b]pyridin-2(3H)-one (I-27)

$^1$H-NMR ((CD$_3$)$_2$SO) δ 10.74 (s, 1H), 8.23 (d, J=3.5 Hz, 1H), 8.17 (s, 1H), 7.93 (d, J=1.6 Hz, 1H), 7.45 (s, 1H), 6.73 (dd, J=3.5, 1.7 Hz, 1H), 2.43 (s, 3H), 2.33 (s, 3H).

<Example 8-28> Preparation of (Z)-3-(Furan-3-ylmethylene)-5-hydroxy-4,6-dimethyl-1H-pyrrolo[2,3-b]pyridin-2(3H)-one (I-28)

$^1$H-NMR (CD$_3$OD) δ 10.77 (s, 1H), 8.78-8.64 (m, 1H), 8.20 (s, 1H), 7.76 (t, J=1.5 Hz, 1H), 7.52 (s, 1H), 7.40 (d, J=1.6 Hz, 1H), 2.43 (s, 3H), 2.31 (s, 3H).

<Example 8-29> Preparation of (Z)-5-Hydroxy-4,6-dimethyl-3-(thiophen-2-ylmethylene)-1H-pyrrolo[2,3-b]pyridin-2(3H)-one (I-29)

$^1$H-NMR ((CD$_3$)$_2$SO) δ 10.82 (s, 1H), 8.25 (br s, 1H), 7.96 (s, 1H), 7.92 (d, J=3.0 Hz, 1H), 7.87 (d, J=5.1 Hz, 1H), 7.21 (dd, J=5.1, 3.7 Hz, 1H), 2.48 (s, 3H), 2.33 (s, 3H).

<Example 8-30> Preparation of (Z)-5-Hydroxy-4,6-dimethyl-3-((3-methylthiophen-2-yl)methylene)-1H-pyrrolo[2,3-b]pyridin-2(3H)-one (I-30)

$^1$H-NMR (CD$_3$OD) δ 8.18 (s, 1H), 7.82 (d, J=5.1 Hz, 1H), 7.11 (d, J=5.1 Hz, 1H), 2.73 (s, 3H), 2.54 (s, 6H).

<Example 8-31> Preparation of (Z)-5-Hydroxy-4,6-dimethyl-3-(thiophen-2-ylmethylene)-1H-pyrrolo[2,3-b]pyridin-2(3H)-one (I-31)

$^1$H-NMR (CD$_3$OD) δ 8.15 (s, 1H), 7.78 (d, J=3.8 Hz, 1H), 6.97 (dd, J=3.8, 0.9 Hz, 1H), 2.71 (s, 3H), 2.58 (s, 3H), 2.54 (s, 3H).

<Example 8-32> Preparation of (Z)-3-((1H-Pyrrol-3-yl)methylene)-5-hydroxy-4,6-dimethyl-1H-pyrrolo[2,3-b]pyridin-2(3H)-one (I-32)

$^1$H-NMR ((CD$_3$)$_2$SO) δ 13.18 (s, 1H), 11.53 (s, 1H), 7.72 (s, 1H), 7.38 (s, 1H), 7.03 (s, 1H), 6.40-6.34 (m, 1H), 2.53 (s, 3H), 2.40 (s, 3H).

<Example 8-33> Preparation of (Z)-3-((1H-Imidazol-2-yl)methylene)-5-hydroxy-4,6-dimethyl-1H-pyrrolo[2,3-b]pyridin-2(3H)-one (I-33)

$^1$H-NMR ((CD$_3$)$_2$SO) δ 14.91 (br s, 1H), 11.66 (s, 1H), 8.62 (s, 1H), 7.85 (d, J=1.1 Hz, 2H), 7.76 (s, 1H), 2.46 (s, 3H), 2.37 (s, 3H).

<Example 8-34> Preparation of (Z)-3-((1H-Imidazol-4-yl)methylene)-5-hydroxy-4,6-dimethyl-1H-pyrrolo[2,3-b]pyridin-2(3H)-one (I-34)

$^1$H-NMR ((CD$_3$)$_2$SO) δ 13.67 (s, 1H), 11.06 (s, 1H), 7.95 (s, 1H), 7.74 (s, 1H), 7.67 (s, 1H), 2.45 (s, 3H), 2.33 (s, 3H).

<Example 8-35> Preparation of (Z)-5-Hydroxy-4,6-dimethyl-3-(thiazol-2-ylmethylene)-1H-pyrrolo[2,3-b]pyridin-2(3H)-one (I-35)

$^1$H-NMR ((CD$_3$)$_2$SO) δ 10.99 (s, 1H), 8.31 (s, 1H), 8.09 (d, J=3.1 Hz, 1H), 8.00 (d, J=3.1 Hz, 1H), 7.96 (s, 1H), 2.48 (s, 3H), 2.35 (s, 3H).

<Example 8-36> Preparation of (Z)-3-((3,5-Dimethyl-1H-pyrrol-2-yl)methylene)-5-hydroxy-4,6-dimethyl-1H-pyrrolo[2,3-b]pyridin-2(3H)-one (I-36)

$^1$H-NMR ((CD$_3$)$_2$SO) δ 13.26 (s, 1H), 10.99 (s, 1H), 8.13 (s, 1H), 7.43 (s, 1H), 6.00 (d, J=2.2 Hz, 1H), 2.46 (s, 3H), 2.33 (s, 3H), 2.31 (s, 3H), 2.23 (s, 3H).

<Example 8-37> Preparation of (Z)-5-((5-Hydroxy-4,6-dimethyl-2-oxo-1H-pyrrolo[2,3-b]pyridin-3(2H)-ylidene)methyl)-2,4-dimethyl-1H-pyrrole-3-carboxylic acid (I-37)

$^1$H-NMR ((CD$_3$)$_2$SO) δ 13.72 (s, 1H), 12.08 (br s, 1H), 11.11 (s, 1H), 8.17 (br s, 1H), 7.49 (s, 1H), 2.52 (s, 3H), 2.47 (s, 3H), 2.42 (s, 3H), 2.33 (s, 3H).

<Example 8-38> Preparation of ((Z)-Ethyl-5-((5-hydroxy-4,6-dimethyl-2-oxo-1H-pyrrolo[2,3-b]pyridin-3(2H)-ylidene)methyl)-2,4-dimethyl-1H-pyrrole-3-carboxylate (I-38)

$^1$H-NMR ((CD$_3$)$_2$SO) δ 13.8 (s, 1H), 11.19 (br s, 1H), 8.25 (br s, 1H), 7.48 (s, 1H), 4.25-4.13 (m, 2H), 2.50-2.46 (m, 6H), 2.42 (s, 3H), 2.33 (s, 3H), 1.33-1.25 (m, 3H).

<Example 8-39> Preparation of (Z)—N-(2-(Diethylamino)ethyl)-5-((5-hydroxy-4,6-dimethyl-2-oxo-1H-pyrrolo[2,3-b]pyridin-3(2H)-ylidene)methyl)-2,4-dimethyl-1H-pyrrole-3-carboxamide (I-39)

$^1$H-NMR ((CD$_3$)$_2$SO) δ 13.50 (s, 1H), 11.03 (s, 1H), 8.13 (br s, 1H), 7.42 (s, 1H), 7.36 (t, J=5.2 Hz, 1H), 3.30-3.21 (m, 2H), 2.50-2.37 (m, 12H), 2.30 (s, 6H), 0.95 (t, J=7.0 Hz, 6H).

<Example 8-40> Preparation of (Z)—N-(2-(Ethylamino)ethyl)-5-((5-hydroxy-4,6-dimethyl-2-oxo-1H-pyrrolo[2,3-b]pyridin-3(2H)-ylidene)methyl)-2,4-dimethyl-1H-pyrrole-3-carboxamide (I-40)

$^1$H-NMR (CD$_3$OD) δ 13.30 (s, 1H), 7.76 (s, 1H), 3.69 (s, 2H), 3.25 (s, 2H), 3.13 (s, 2H), 2.71 (s, 3H), 2.56-2.38 (m, 9H), 1.35 (s, 3H).

<Example 8-41> Preparation of (Z)—N-Cyclohexyl-5-((5-hydroxy-4,6-dimethyl-2-oxo-1H-pyrrolo[2,3-b]pyridin-3(2H)-ylidene)methyl)-2,4-dimethyl-1H-pyrrole-3-carboxamide (I-41)

$^1$H-NMR ((CD$_3$)$_2$SO) δ 13.49 (s, 1H), 11.08 (br s, 1H), 8.21 (br s, 1H), 7.55 (d, J=8.0 Hz, 1H), 7.45 (s, 1H), 3.78-3.62 (m, 1H), 2.46 (s, 3H), 2.40 (s, 3H), 2.33 (s, 3H), 2.29 (s, 3H), 1.85-1.66 (m, 4H), 1.63-1.53 (m, 1H), 1.36-1.07 (m, 5H).

<Example 8-42> Preparation of (Z)-5-((5-Hydroxy-4,6-dimethyl-2-oxo-1H-pyrrolo[2,3-b]pyridin-3(2H)-ylidene)methyl)-2,4-dimethyl-N-(2-(piperidin-1-yl)ethyl)-1H-pyrrole-3-carboxamide (I-42)

$^1$H-NMR ((CD$_3$)$_2$SO) δ 13.54 (s, 1H), 7.48-7.42 (m, 2H), 3.35-3.25 (m, 2H), 2.46 (s, 3H), 2.43 (s, 3H), 2.40-2.24 (m, 12H), 1.55-1.27 (m, 6H).

<Example 8-43> Preparation of (Z)-3-((3,5-Dimethyl-4-(piperidine-1-carbonyl)-1H-pyrrol-2-yl)methylene)-5-hydroxy-4,6-dimethyl-1H-pyrrolo[2,3-b]pyridin-2(3H)-one (I-43)

$^1$H-NMR ((CD$_3$)$_2$SO) δ 13.46 (s, 1H), 11.09 (s, 1H), 8.21 (br s, 1H), 7.43 (s, 1H), 3.60-3.40 (m, 4H), 2.46 (s, 3H), 2.33 (s, 3H), 2.27 (s, 3H), 2.17 (s, 3H), 1.65-1.36 (m, 6H).

<Example 8-44> Preparation of (Z)-3-((3,5-Dimethyl-4-(pyrrolidine-1-carbonyl)-1H-pyrrol-2-yl)methylene)-5-hydroxy-4,6-dimethyl-1H-pyrrolo[2,3-b]pyridin-2(3H)-one (I-44)

$^1$H-NMR ((CD$_3$)$_2$SO) δ 13.43 (s, 1H), 11.09 (s, 1H), 8.18 (s, 1H), 7.43 (s, 1H), 3.51-3.40 (m, 2H), 3.27-3.18 (m, 2H), 2.46 (s, 3H), 2.33 (s, 3H), 2.29 (s, 3H), 2.19 (s, 3H), 1.92-1.74 (m, 4H).

<Example 8-45> Preparation of (Z)-3-((3,5-Dimethyl-4-(4-methylpiperazine-1-carbonyl)-1H-pyrrol-2-yl)methylene)-5-hydroxy-4,6-dimethyl-1H-pyrrolo[2,3-b]pyridin-2(3H)-one (I-45)

$^1$H-NMR ((CD$_3$)$_2$SO) δ 13.49 (s, 1H), 11.11 (s, 1H), 8.21 (br s, 1H), 7.45 (s, 1H), 3.49-3.35 (m, 4H), 2.47 (s, 3H), 2.33 (s, 3H), 2.31-2.27 (m, 7H), 2.21-2.17 (m, 6H).

<Example 8-46> Preparation of (Z)-3-((3,5-Dimethyl-4-(morpholine-4-carbonyl)-1H-pyrrol-2-yl)methylene)-5-hydroxy-4,6-dimethyl-1H-pyrrolo[2,3-b]pyridin-2(3H)-one (I-46)

$^1$H-NMR ((CD$_3$)$_2$SO) δ 13.49 (s, 1H), 11.10 (s, 1H), 8.19 (br s, 1H), 7.43 (s, 1H), 3.62-3.54 (m, 4H), 3.53-3.39 (m, 4H), 2.46 (s, 3H), 2.33 (s, 3H), 2.29 (s, 3H), 2.20 (s, 3H).

<Experimental Example 1> Cytotoxicity Test

A cytotoxicity test was measured by MTT assay. Each cell line was cultured in a 96-well plate at a density of $1 \times 10^4$ cells/well. After 24 hours, the culture medium containing 1% FBS (fetal bovine serum) was treated and reacted with compounds or solutions of compounds for 48 hours.

MTT (3-(4,5-dimethylthiazol-2-yl)-2,5-diphenyltetrazolium bromide) solution (5 mg/mL) was added to each well and reacted for 4 hours in an incubator. Finally, the medium containing the MTT solution was discarded and DMSO was added to dissolve formazan (5-(4,5-dimethylthiazol-2-yl)-1,3-diphenylformazan) formed in the cells. After reacting in an incubator for 30 minutes, the formation of formazan was quantified using a microplate reader at an absorbance of 540 nm.

First, the cytotoxicity of each compound was examined by treating the compound with MCF-7 (human breast cancer cell line) and PANC-1 (human pancreatic cancer cell line) having a concentration of 30 μM to search for compounds that are effective in cancer cell death. At this time, sunitinib was used as a control group. The results of the cytotoxicity test are shown in Tables 2 and 3 below.

Compounds showing cytotoxicity equal or more than 70% against MCF-7 cells, compounds showing better inhibitory activity than sunitinib, and especially significant meaningful compounds in terms of chemical structure were selected to measure cytotoxicity $IC_{50}$ in 8 different human cancer cell lines. The human cancer cell lines used herein are MCF-7 (breast cancer), MDA-MB-231 (breast cancer), HT-29 (colon cancer), DU145 (prostate cancer), U937 (myeloid leukemia), A549 (lung cancer), PANC-1 (pancreatic cancer) and MIA PaCa-2 (pancreatic cancer). The results of measurement are shown in Tables 4 to 11 below.

The compounds showing cytotoxicity greater than or equal to that of the reference drug sunitinib against each cancer cell line were I-19, I-24, I-39, I-40, and I-41 against MCF-7, I-24, I-39, I-40 and I-41 against MDA-MB-231, I-24, I-40 and I-41 against HT-29, I-15, I-17, I-18, I-22, I-24, I-39, I-40 and I-41 against DU-145, I-24 and I-41 against U937, and I-24, I-40 and I-41 against A-549. PANC-1 and MIA PaCa-2 cell lines, pancreatic cancer cell lines, were found to have resistance to gemcitabine as shown in Tables 10 and 11 below. The compounds showing cytotoxicity greater than or equal to that of the reference drug sunitinib against these cell lines were I-18, I-19, I-24, I-39, I-40, I-41 and I-46 against PANC-1 and I-39, I-40 and I-41 against MIA PaCa-2. The cytotoxicity $IC_{50}$ of 20 compounds including the above compounds was measured for HEK293 (human embryonic kidney cell line) and CHO-K1 (silkworm ovary cell), which are normal cell lines. The results of measurement are shown in Tables 12 and 13 below.

All of the 20 compounds showed higher $IC_{50}$ values than sunitinib against HEK293 and CHO-K1 cells, indicating that they are safer compounds than sunitinib.

TABLE 2

Cytotoxicity against MCF-7 at 30 μM (48 h)

| Compounds | Cell viability (% inhibition) |
|---|---|
| Sunitinib | 92.6 |
| I-01 | 76.9 |
| I-02 | 30.5 |
| I-03 | 6.6 |
| I-04 | 6.9 |
| I-05 | 10.0 |
| I-06 | 32.3 |
| I-07 | 23.9 |
| I-08 | 16.3 |
| I-09 | 48.3 |
| I-10 | 51.7 |
| I-11 | 29.2 |
| I-12 | 30.7 |
| I-13 | 29.6 |
| I-14 | 23.9 |
| I-15 | 67.5 |
| I-16 | 41.2 |

TABLE 2-continued

Cytotoxicity against MCF-7 at 30 μM (48 h)

| Compounds | Cell viability (% inhibition) |
|---|---|
| I-17 | 74.7 |
| I-18 | 62.5 |
| I-19 | 78.1 |
| I-20 | 30.5 |
| I-21 | 28.1 |
| I-22 | 78.0 |
| I-23 | 63.2 |
| I-24 | 82.3 |
| I-25 | 14.5 |
| I-26 | 2.4 |
| I-27 | 31.5 |
| I-28 | 66.3 |
| I-29 | 57.8 |
| I-30 | 59.0 |
| I-31 | 53.4 |
| I-32 | 27.0 |
| I-33 | 2.6 |
| I-34 | 4.1 |
| I-35 | 5.6 |
| I-36 | 47.3 |
| I-37 | 60.4 |
| I-38 | 41.7 |
| I-39 | 62.7 |
| I-41 | 78.1 |
| I-42 | 63.4 |
| I-43 | 50.5 |
| I-44 | 47.7 |
| I-45 | 60.7 |
| I-46 | 71.2 |

TABLE 3

Cytotoxicity against PANC-1 at 30 μM (48 h)

| Compounds | Cell viability (% inhibition) |
|---|---|
| Sunitinib | 64.5 |
| I-01 | 77.4 |
| I-02 | 44.9 |
| I-03 | 37.5 |
| I-04 | 24.4 |
| I-05 | 49.0 |
| I-06 | 29.1 |
| I-07 | 27.8 |
| I-08 | 32.5 |
| I-09 | 51.8 |
| I-10 | 44.9 |
| I-11 | 42.0 |
| I-12 | 10.2 |
| I-13 | 46.4 |
| I-14 | 36.3 |
| I-15 | 69.2 |
| I-16 | 40.6 |
| I-17 | 71.7 |
| I-18 | 66.3 |
| I-19 | 81.4 |
| I-20 | 28.9 |
| I-21 | 29.2 |
| I-22 | 72.7 |
| I-23 | 65.4 |
| I-24 | 82.2 |
| I-25 | 32.3 |
| I-26 | 17.1 |
| I-27 | 16.4 |
| I-28 | 26.1 |
| I-29 | 42.2 |
| I-30 | 47.2 |
| I-31 | 30.1 |
| I-32 | 16.9 |
| I-33 | 7.2 |
| I-34 | 4.5 |

TABLE 3-continued

Cytotoxicity against PANC-1 at 30 μM (48 h)

| Compounds | Cell viability (% inhibition) |
|---|---|
| I-35 | 9.0 |
| I-36 | 44.7 |
| I-37 | 55.8 |
| I-38 | 35.7 |
| I-39 | 69.6 |
| I-41 | 78.3 |
| I-42 | 70.7 |
| I-43 | 38.5 |
| I-44 | 31.8 |
| I-45 | 48.7 |
| I-46 | 71.1 |

TABLE 4

Cytotoxicity against MCF-7 ($IC_{50}$, 48 h)

| Compounds | $IC_{50}$ (μM) |
|---|---|
| Sunitinib | 7.30 |
| I-01 | 13.85 |
| I-15 | 20.88 |
| I-17 | 11.02 |
| I-18 | 13.23 |
| I-19 | 6.37 |
| I-22 | 17.40 |
| I-23 | 19.05 |
| I-24 | 2.04 |
| I-28 | 22.87 |
| I-36 | 31.62 |
| I-37 | 14.79 |
| I-38 | 39.81 |
| I-39 | 6.09 |
| I-40 | 1.32 |
| I-41 | 6.90 |
| I-42 | 8.70 |
| I-43 | 26.91 |
| I-44 | 34.67 |
| I-45 | 10.23 |
| I-46 | 12.64 |

TABLE 5

Cytotoxicity against MBA-MB-231 ($IC_{50}$, 48 h)

| Compounds | $IC_{50}$ (μM) |
|---|---|
| Sunitinib | 6.09 |
| I-01 | 12.63 |
| I-15 | 22.87 |
| I-17 | 10.53 |
| I-18 | 12.07 |
| I-19 | 22.87 |
| I-22 | 9.61 |
| I-24 | 2.81 |
| I-36 | 10.23 |
| I-37 | 19.49 |
| I-38 | 24.54 |
| I-39 | 5.31 |
| I-40 | 1.47 |
| I-41 | 3.52 |
| I-42 | 8.12 |
| I-43 | 14.79 |
| I-44 | 43.65 |
| I-45 | 16.21 |
| I-46 | 14.49 |

TABLE 6

Cytotoxicity against HT-29 ($IC_{50}$, 48 h)

| Compounds | $IC_{50}$ (μM) |
|---|---|
| Sunitinib | 4.89 |
| I-01 | 12.88 |
| I-15 | 16.62 |
| I-17 | 25.12 |
| I-18 | 36.30 |
| I-19 | 11.53 |
| I-22 | 19.95 |
| I-23 | 30.08 |
| I-24 | 4.57 |
| I-36 | 16.62 |
| I-37 | 26.24 |
| I-38 | 22.88 |
| I-39 | 20.89 |
| I-40 | 1.45 |
| I-41 | 4.47 |
| I-42 | 15.17 |
| I-43 | 16.62 |
| I-44 | 43.35 |
| I-45 | 36.12 |
| I-46 | 57.54 |

TABLE 7

Cytotoxicity against DU145 ($IC_{50}$, 48 h)

| Compounds | $IC_{50}$ (μM) |
|---|---|
| Sunitinib | 5.88 |
| I-01 | 10.97 |
| I-15 | 5.55 |
| I-17 | 4.57 |
| I-18 | 1.14 |
| I-19 | 8.77 |
| I-22 | 1.18 |
| I-23 | 30.08 |
| I-24 | 1.07 |
| I-28 | 22.87 |
| I-39 | 2.88 |
| I-40 | 0.26 |
| I-41 | <1.00 |
| I-46 | 22.90 |

TABLE 8

Cytotoxicity against U937 ($IC_{50}$, 48 h)

| Compounds | $IC_{50}$ (μM) |
|---|---|
| Sunitinib | 6.98 |
| I-01 | 11.54 |
| I-15 | 32.96 |
| I-17 | 12.64 |
| I-19 | 16.62 |
| I-22 | 14.49 |
| I-23 | 34.50 |
| I-24 | 6.67 |
| I-28 | 31.49 |
| I-36 | 33.88 |
| I-37 | 14.79 |
| I-38 | 12.88 |
| I-39 | 8.01 |
| I-41 | 3.21 |
| I-42 | 14.79 |
| I-43 | 9.77 |
| I-44 | 52.48 |
| I-45 | 26.24 |

TABLE 9

Cytotoxicity against A549 (IC$_{50}$, 48 h)

| Compounds | IC$_{50}$ (μM) |
|---|---|
| Sunitinib | 6.98 |
| I-01 | 7.60 |
| I-15 | 47.49 |
| I-17 | 10.05 |
| I-18 | 13.22 |
| I-19 | 31.47 |
| I-22 | 13.84 |
| I-23 | 30.08 |
| I-24 | 4.20 |
| I-36 | 13.86 |
| I-37 | 19.95 |
| I-38 | 18.19 |
| I-39 | 19.95 |
| I-40 | 1.47 |
| I-41 | 6.08 |
| I-42 | 13.24 |
| I-43 | 12.07 |
| I-44 | 50.11 |
| I-45 | 26.30 |
| I-46 | 30.08 |

TABLE 10

Cytotoxicity against PANC-1 (IC$_{50}$, 48 h)

| Compounds | IC$_{50}$ (μM) |
|---|---|
| Sunitinib | 15.48 |
| Gemcitabine | >1000 |
| I-15 | 19.49 |
| I-18 | 13.8 |
| I-19 | 7.41 |
| I-23 | 19.05 |
| I-24 | 4.26 |
| I-39 | 15.13 |
| I-40 | 1.02 |
| I-41 | 5.88 |
| I-46 | 11.48 |

TABLE 11

Cytotoxicity against MIA PaCa-2 (IC$_{50}$, 48 h)

| Compounds | IC$_{50}$ (μM) |
|---|---|
| Sunitinib | 8.51 |
| Gemcitabine | >1000 |
| I-18 | 11.48 |
| I-39 | 7.94 |
| I-40 | 1.58 |
| I-41 | 5.01 |

TABLE 12

Cytotoxicity against HEK293 (IC$_{50}$, 48 h)

| Compounds | IC$_{50}$ (μM) |
|---|---|
| Sunitinib | 7.30 |
| Doxorubicin | 0.32 |
| I-01 | >90 |
| I-15 | 37.80 |
| I-17 | 32.96 |
| I-18 | >90 |
| I-19 | 26.23 |
| I-22 | >90 |
| I-23 | 45.70 |
| I-24 | 46.77 |
| I-28 | 19.95 |
| I-36 | >90 |
| I-37 | 38.01 |
| I-38 | >90 |
| I-39 | 40.73 |
| I-40 | 19.05 |
| I-41 | 37.15 |
| I-42 | 21.37 |
| I-43 | >90 |
| I-44 | >90 |
| I-45 | 38.01 |
| I-46 | >90 |

TABLE 13

Cytotoxicity against CHO-K1 (IC$_{50}$, 48 h)

| Compounds | IC$_{50}$ (μM) |
|---|---|
| Sunitinib | 20.87 |
| Doxorubicin | 12.07 |
| I-01 | 20.88 |
| I-15 | 47.49 |
| I-17 | 30.08 |
| I-18 | >90 |
| I-19 | 30.08 |
| I-22 | 78.48 |
| I-23 | 57.01 |
| I-24 | 54.46 |
| I-28 | >90 |
| I-36 | 50.11 |
| I-37 | 33.11 |
| I-38 | 23.98 |
| I-39 | >90 |
| I-40 | 40.73 |
| I-41 | 43.35 |
| I-42 | 51.28 |
| I-43 | 14.79 |
| I-44 | 58.88 |
| I-45 | 23.44 |
| I-46 | >90 |

INDUSTRIAL APPLICABILITY

The 7-azaindolin-2-one derivatives or pharmaceutically acceptable salts thereof according to the present invention can be favorably used as a medicament for inhibiting cancer growth and cancer metastasis.

The invention claimed is:

1. A compound represented by the following Formula 1 or a pharmaceutically acceptable salt thereof:

[Formula 1]

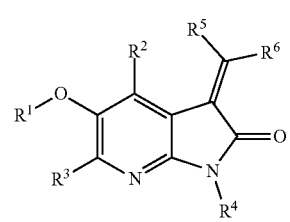

wherein, $R^1$, $R^4$ and $R^5$ each independently represent any one selected from the group consisting of hydrogen; halogen; and $C_1$-$C_4$ alkyl;

$R^2$ and $R^3$ each independently represent $C_1$-$C_4$ alkyl;

$R^6$ represents any one selected from the group consisting of hydrogen; $C_1$-$C_{12}$ alkyl; $C_2$-$C_{12}$ alkenyl; $C_6$-$C_{12}$ aryl; and $C_3$-$C_{12}$ heteroaryl containing 1 to 3 heteroatoms;

wherein the $C_1$-$C_{12}$ alkyl or the $C_2$-$C_{12}$ alkenyl is unsubstituted or substituted with $C_6$-$C_{12}$ aryl;

the $C_6$-$C_{12}$ aryl represented by $R^6$ is unsubstituted or substituted with one or more substituents selected from the group consisting of halogen; —$NO_2$; $C_1$-$C_4$ alkyl; —$OR^{11}$; and —$NR^{20}R^{21}$;

the $C_3$-$C_{12}$ heteroaryl is unsubstituted or substituted with one or more substituents selected from the group consisting of $C_1$-$C_4$ alkyl; —$C(O)R^{14}$; —$C(O)OR^{15}$; and —$C(O)NR^{22}R^{23}$;

$R^{11}$, $R^{14}$ and $R^{15}$ each independently represent hydrogen or $C_1$-$C_4$ alkyl;

$R^{20}$, $R^{21}$, $R^{22}$ and $R^{23}$ each independently represent hydrogen or $C_1$-$C_6$ alkyl, or $R^{22}$ and $R^{23}$ taken together form $C_3$-$C_8$ heterocycle containing 1 to 3 heteroatoms;

wherein the $C_1$-$C_4$ alkyl and the $C_3$-$C_8$ heterocycle of $R^{11}$, $R^{14}$, $R^{15}$, and $R^{20}$ to $R^{23}$ are each independently unsubstituted or substituted with one or more substituents selected from the group consisting of $C_1$-$C_4$ alkyl; and —$NR^{24}R^{25}$;

$R^{24}$ and $R^{25}$ each independently represent any one selected from the group consisting of hydrogen; and $C_1$-$C_4$ alkyl, or $R^{24}$ and $R^{25}$ taken together form $C_3$-$C_8$ heterocycle containing 1 to 3 heteroatoms.

2. The compound or the pharmaceutically acceptable salt thereof according to claim 1, wherein $R^1$, $R^4$ are $R^5$ are hydrogen; and $R^2$ and $R^3$ are methyl.

3. The compound or the pharmaceutically acceptable salt thereof according to claim 1, wherein $R^6$ represents:

hydrogen; or $C_1$-$C_{12}$ alkyl or $C_2$-$C_{12}$ alkenyl which is unsubstituted or substituted with $C_6$-$C_{12}$ aryl, wherein said $C_6$-$C_{12}$ aryl is unsubstituted or substituted with one or more substituents selected from the group consisting of OH and methoxy; or $C_6$-$C_{12}$ aryl which is unsubstituted or substituted with one or more substituents selected from the group consisting of halogen, —$NO_2$, OH, methoxy, methyl, ethyl, propyl, methylamine, ethylamine, dimethylamine and diethylamine; or $C_3$-$C_{12}$ heteroaryl containing 1 to 3 heteroatoms which is unsubstituted or substituted with one or more substituents selected from the group consisting of methyl; ethyl; —$C(O)OR^{15}$; and —$C(O)NR^{22}R^{23}$;

$R^{15}$ represents hydrogen, methyl or ethyl;

$R^{22}$ and $R^{23}$ each independently represent hydrogen; or methyl or ethyl, which is unsubstituted or substituted with one or more substituents selected from the group consisting of methylamine, ethylamine, dimethylamine, diethylamine and piperidine; or $R^{22}$ and $R^{23}$ taken together form piperazine, piperidine, pyrrolidine or morpholine unsubstituted or substituted with methyl.

4. The compound or the pharmaceutically acceptable salt thereof according to claim 1, wherein $R^6$ represents:

$C_1$-$C_8$ alkyl which is unsubstituted or substituted with one or more phenyls; or $C_2$-$C_8$ alkenyl which is unsubstituted or substituted with phenyl, wherein said phenyl is unsubstituted or substituted with one or more substituents selected from the group consisting of OH and methoxy; or $C_6$-$C_{10}$ aryl which is unsubstituted or substituted with one or more substituents selected from the group consisting of halogen, —$NO_2$, OH, methoxy, methyl, ethyl, dimethylamine and diethylamine; or $C_3$-$C_{10}$ heteroaryl containing 1 to 3 heteroatoms which is unsubstituted or substituted with one or more substituents selected from the group consisting of methyl; ethyl; —$C(O)OR^{15}$; and —$C(O)NR^{22}R^{23}$;

$R^{15}$ represents hydrogen, methyl or ethyl;

$R^{22}$ and $R^{23}$ each independently represent hydrogen; or methyl or ethyl, which is unsubstituted or substituted with one or more substituents selected from the group consisting of methylamine, ethylamine, dimethylamine, diethylamine and piperidine; or $R^{22}$ and $R^{23}$ taken together form piperazine, piperidine, pyrrolidine or morpholine unsubstituted or substituted with methyl.

5. The compound or the pharmaceutically acceptable salt thereof according to claim 1, wherein the compound represented by Formula 1 is any one selected from the group consisting of the compounds represented by the following Formulas I-01 to I-46:

[Formula I-01]

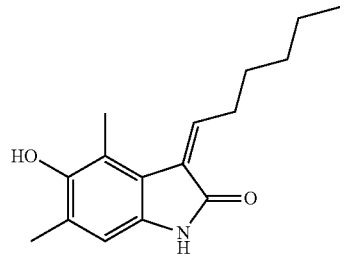

[Formula I-02]

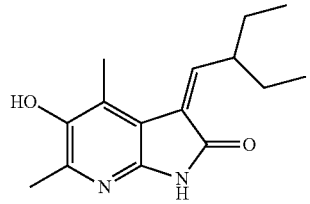

[Formula I-03]

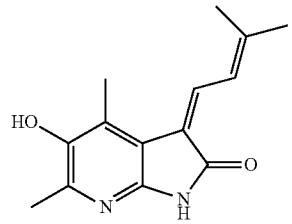

[Formula I-04]

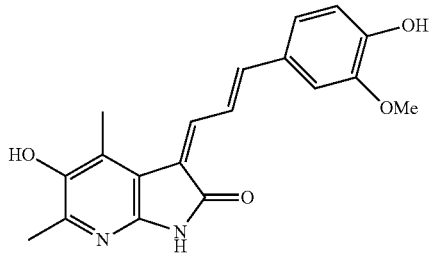

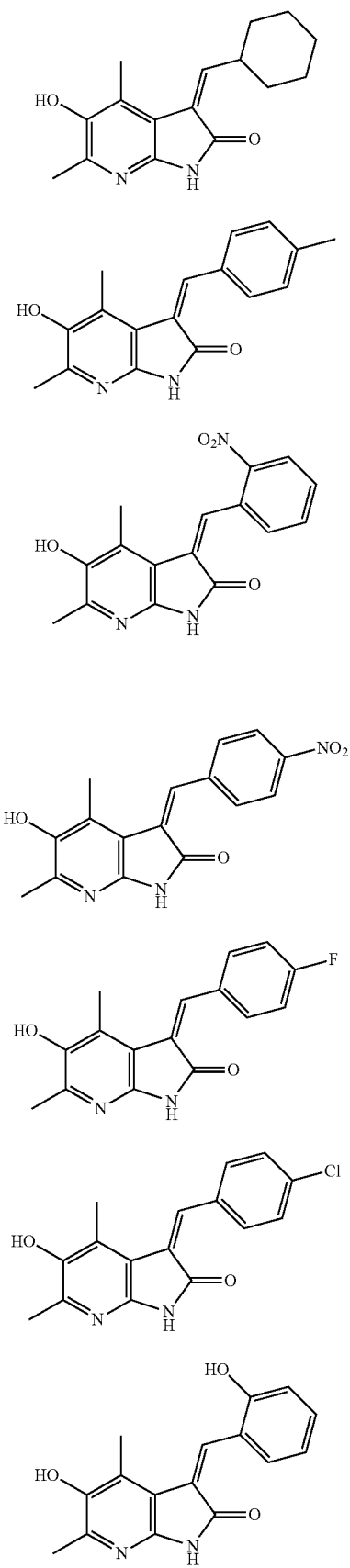
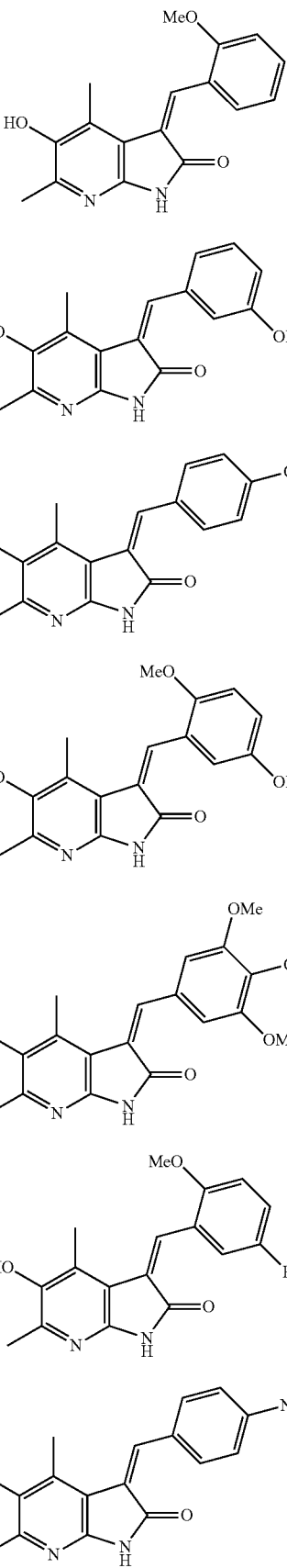

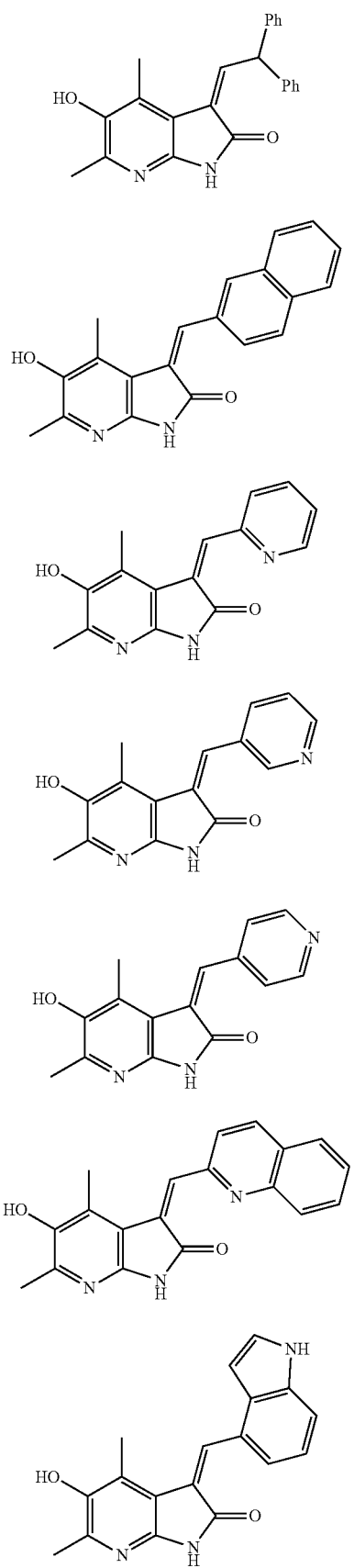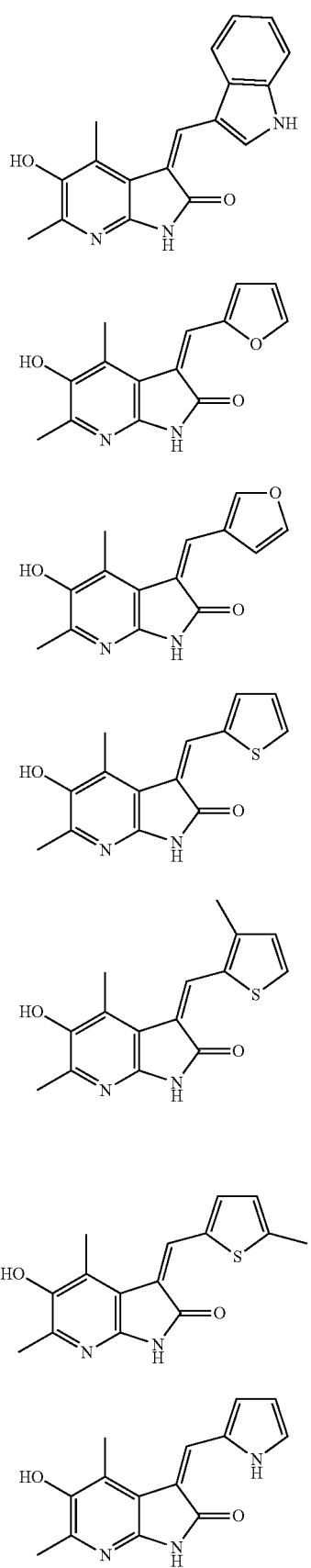

[Formula I-33]
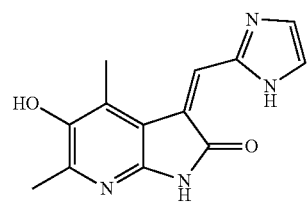
[Formula I-34]
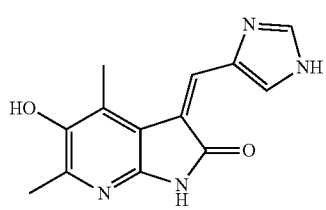
[Formula I-35]
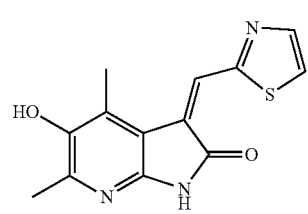
[Formula I-36]
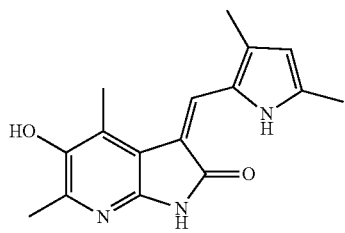
[Formula I-37]
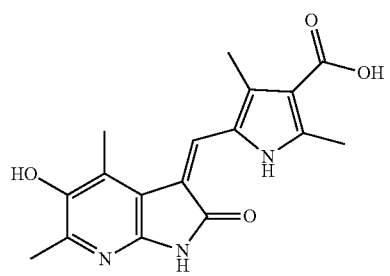
[Formula I-38]
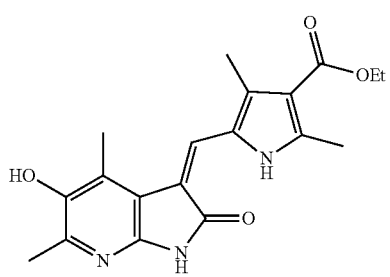
[Formula I-39]
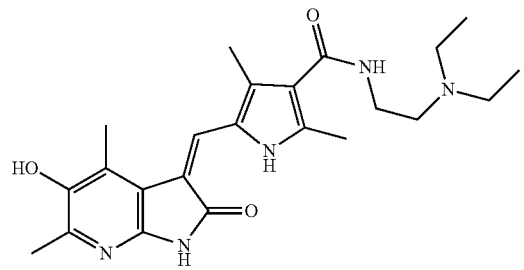
[Formula I-40]
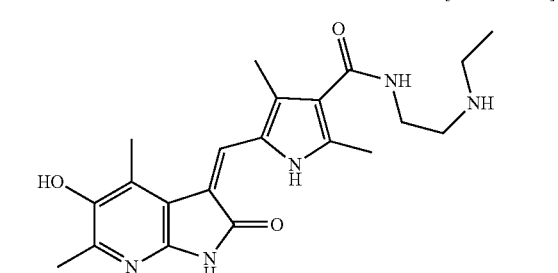
[Formula I-41]
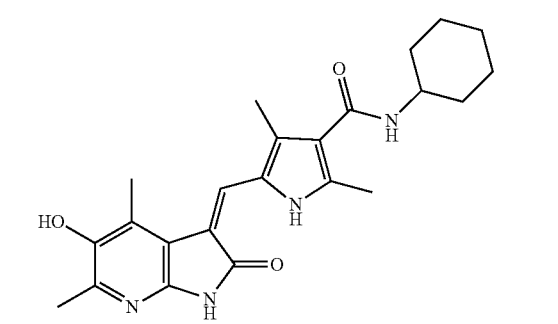
[Formula I-42]
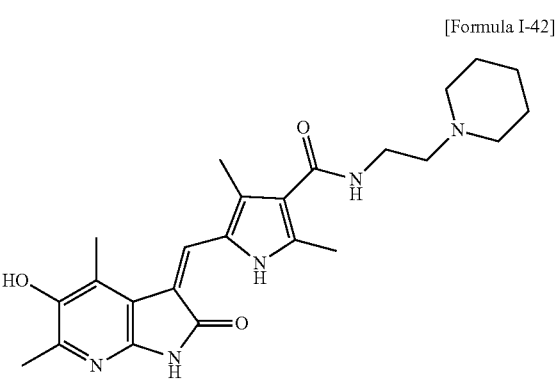
[Formula I-43]
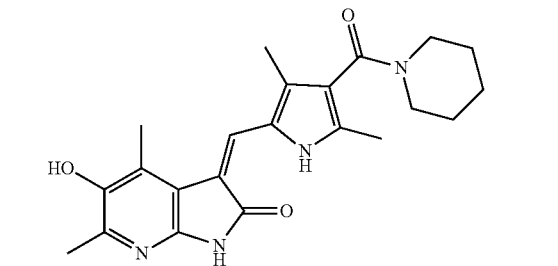

[Formula I-44]

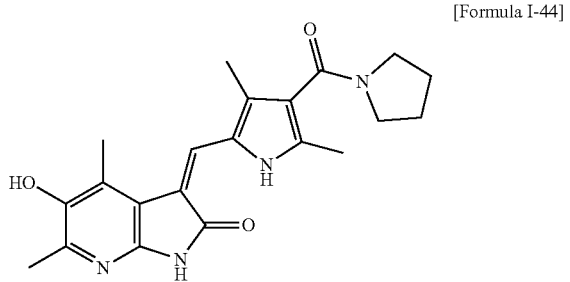

[Formula I-45]

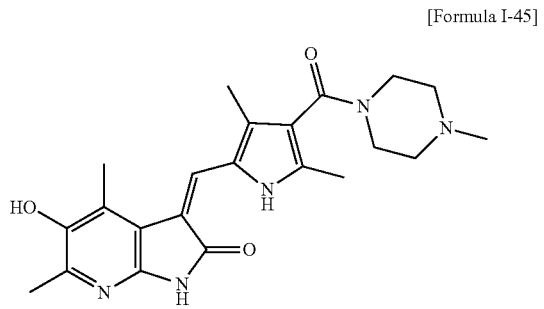

[Formula I-46]

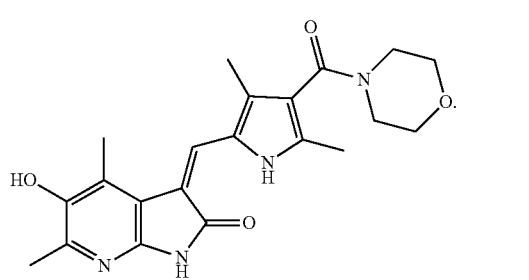

6. The compound or the pharmaceutically acceptable salt thereof according to claim 1, wherein the pharmaceutically acceptable salt is in the form of an acid addition salt that is formed by an organic acid selected from the group consisting of oxalic acid, maleic acid, fumaric acid, malic acid, tartaric acid, citric acid and benzoic acid, or an inorganic acid selected from the group consisting of hydrochloric acid, sulfuric acid, phosphoric acid and hydrobromic acid.

7. A method for preparing a compound of the following Formula 1, comprising reacting a compound of the following Formula 2 with a compound of the following Formula 3:

[Formula 2]

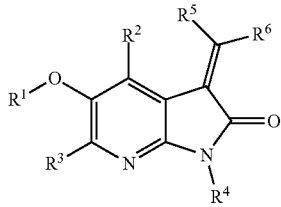

[Formula 3]

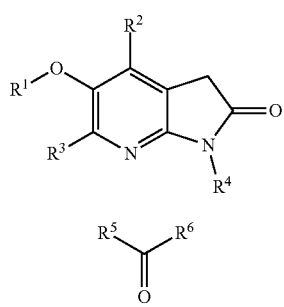

[Formula 1]

wherein, $R^1$, $R^4$ and $R^5$ each independently represent any one selected from the group consisting of hydrogen; halogen; and $C_1$-$C_4$ alkyl;

$R^2$ and $R^3$ each independently represent $C_1$-$C_4$ alkyl;

$R^6$ represents any one selected from the group consisting of hydrogen; $C_1$-$C_{12}$ alkyl; $C_2$-$C_{12}$ alkenyl; $C_6$-$C_{12}$ aryl; and $C_3$-$C_{12}$ heteroaryl containing 1 to 3 heteroatoms;

wherein the $C_1$-$C_{12}$ alkyl or the $C_2$-$C_{12}$ alkenyl is unsubstituted or substituted with $C_6$-$C_{12}$ aryl;

the $C_6$-$C_{12}$ aryl represented by $R^6$ is unsubstituted or substituted with one or more substituents selected from the group consisting of halogen; —$NO_2$; $C_1$-$C_4$ alkyl; —$OR^{11}$; and —$NR^{20}R^{21}$;

the $C_3$-$C_{12}$ heteroaryl is unsubstituted or substituted with one or more substituents selected from the group consisting of $C_1$-$C_4$ alkyl; —$C(O)R^{14}$; —$C(O)OR^{15}$; and —$C(O)NR^{22}R^{23}$;

$R^{11}$, $R^{14}$ and $R^{15}$ each independently represent hydrogen or $C_1$-$C_4$ alkyl;

$R^{20}$, $R^{21}$, $R^{22}$ and $R^{23}$ each independently represent hydrogen or $C_1$-$C_6$ alkyl, or $R^{22}$ and $R^{23}$ taken together form $C_3$-$C_8$ heterocycle containing 1 to 3 heteroatoms;

wherein the $C_1$-$C_4$ alkyl and the $C_3$-$C_8$ heterocycle of $R^{11}$, $R^{14}$, $R^{15}$, and $R^{20}$ to $R^{23}$ are each independently unsubstituted or substituted with one or more substituents selected from the group consisting of $C_1$-$C_4$ alkyl; and —$NR^{24}R^{25}$;

$R^{24}$ and $R^{25}$ each independently represent any one selected from the group consisting of hydrogen; and $C_1$-$C_4$ alkyl, or $R^{24}$ and $R^{25}$ taken together form $C_3$-$C_8$ heterocycle containing 1 to 3 heteroatoms.

8. A pharmaceutical composition for preventing or treating a cancer, comprising the compound or the pharmaceutically acceptable salt thereof according to claim 1 as an active ingredient, wherein the composition comprises at least one of a pharmaceutically acceptable carrier, excipient or a combination thereof, wherein the cancer is any one selected from the group of lung cancer, breast cancer, bladder cancer, bone cancer, thyroid cancer, parathyroid cancer, rectal cancer, prostate cancer, renal cancer, laryngopharyngeal cancer, larynx cancer, esophageal cancer, pancreatic cancer, colorectal cancer, stomach cancer, tongue cancer, skin cancer, brain tumor, uterine cancer, head or neck cancer, gallbladder cancer, oral cancer, colon cancer, anal cancer, tumors of the central nervous system and liver cancer.

* * * * *